United States Patent
Westbrook

(10) Patent No.: US 6,576,421 B1
(45) Date of Patent: *Jun. 10, 2003

(54) METHODS AND COMPOSITIONS FOR THE DETECTION OF CHROMOSOMAL ABERRATIONS

(75) Inventor: Carol A. Westbrook, Chicago, IL (US)

(73) Assignee: ARCH Development Corporation, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/502,954

(22) Filed: Feb. 11, 2000

Related U.S. Application Data

(63) Continuation of application No. 07/784,222, filed on Oct. 28, 1991, now Pat. No. 6,025,126.

(51) Int. Cl.[7] ............................ C12Q 1/68; C12P 19/34; C07H 21/02
(52) U.S. Cl. ........................ 435/6; 435/91.2; 536/23.1; 536/243; 536/24.31; 536/26.6
(58) Field of Search .................. 435/6, 91.2; 536/23.1, 536/24.3, 24.31, 24.33, 26.6

(56) References Cited

U.S. PATENT DOCUMENTS

| | | | |
|---|---|---|---|
| 4,599,305 A | 7/1986 | Witte et al. ..................... | 435/7 |
| 4,681,840 A | 7/1987 | Stephenson et al. ........... | 435/6 |
| 4,711,955 A | 12/1987 | Ward et al. .................... | 536/29 |

(List continued on next page.)

FOREIGN PATENT DOCUMENTS

| | | |
|---|---|---|
| CA | 2021489 | 1/1991 |
| CA | 1301605 | 5/1992 |
| EP | 0 181 635 | 5/1986 |
| EP | 181635 | 5/1986 |
| EP | 0 430 402 | 6/1991 |

(List continued on next page.)

OTHER PUBLICATIONS

Tkacuk et al, "Detection of bcr–abl fusion in chronic myelogenous leukemia by in situ hybridization", Science 250:559–562, Oct. 1990.*
Shtivelman et al, "Alternative splicing of RNAs transcribed from the human abl gene and from the bcr–abl fused gene", Cell 47:277–284, Oct. 1986.*
Hariharan et al, "cDNA sequences for human bcr, the gene that translocates to the abl oncogene in chronic myeloid leukemia", EMBO J. 6(1):115–119, Jan. 1987.*
Stratagene catalog, p. 39, Jan. 1988.*
Rubin et al, "heterogeneity of genomic fusion of BCR and ABL in philadelphia chromosome—positive acute lymphoblastic leukemia" Proc. Natl. Acad. Sci. 85:2795–2799, Apr. 1988.*

Abu–Elheiga, L. et al. (1995) "Human Acetyl–CoA Carboxylase: Characterization, Molecular Cloning, and Evidence For Two Isoforms." *Proc. Natl. Acad. Sci.*, 92:4011–4015.
Albertson, D., et al. (1985) "Mapping Muscle Protein Genes by In Situ Hybridization using Biotin–Labeled Probes." *The EMBO Journal*, 4(10): 2493–2498.
Anastasi, J., et al. (1990) "Detection of Numerical Chromosomal Abnormalities in Neoplastic Hematopoietic Cells by In Situ Hybridization with a Chromosome–Specific Probe." *Am. J. Pathol.*, 136(1): 131–139.
Arnoldus, E.P.J., et al. (1990) "Detection of the Philadelphia Chromosome in Interphase Nuclei." *Cytogenet. Cell Genet.*, 54: 108–111.
Bartram, C., et al. (1987) "Philadelphia–Positive Chronic Myelogenous Leukemia with Breakpoint 5' of the Breakpoint Cluster Region but within the bcr Gene." *Blut*, 55: 505–511.
Benn, P., et al. (1987) "Utility of Molecular Genetic Analysis of bcr Rearrangement in the Diagnosis of Chronic Myeloid Leukemia." *Cancer Genet. Cytogenet.*, 29: 1–7.
Blennerhassett, G., et al. (1988) "Clinical Evaluation of a DNA Probe Assay for the Philadelphia Translocation in Chronic Myelogenous Leukemia." *Leukemia*, 2(10): 648–657.
Brauch, H.,et al. (1987) "Molecular Analysis of the Short Arm of Chromosome 3 in Small–Cell and Non–Small–Cell Carcinoma of the Lung." *N. Engl. J. Med.*, 317(18):1109–1113.
Brock, H., et al. (1981) "Quantitative In Situ Hybridization Reveals Extent of Sequence Homology Between Related DNA Sequences in *Drosophila Melanogaster.*" *Chromosoma*, 83: 159–168.
Callen, D.F., et al. (1992) "High–Resolution Cytogenetic –Based Physical Map of Human Chromosome 16." *Genomics*, 13: 1178–1185.(1992).

(List continued on next page.)

Primary Examiner—Jeffrey Fredman
(74) *Attorney, Agent, or Firm*—Barnes & Thornburg; Alice O. Martin

(57) ABSTRACT

This invention relates generally to methods and compositions for direct detection of specific nucleic acid flanking sequences associated with structural chromosomal aberration breakpoints, by forming hybrids between the sequences and genetic probes, and detecting the probes. In particular aspects, the invention concerns detection of nucleic acid sequences in situ in chromosomes, and more specifically in cells, including interphase cells. Compositions of probes useful for detecting chromosomal translocations, in particular those associated with human leukemias, are also disclosed. An aspect of the invention is labelled probes that, when juxtaposed by formation of an aberration, are distinguishable and provide a pattern different from that of normal cells.

36 Claims, 5 Drawing Sheets

U.S. PATENT DOCUMENTS

Figure 1:
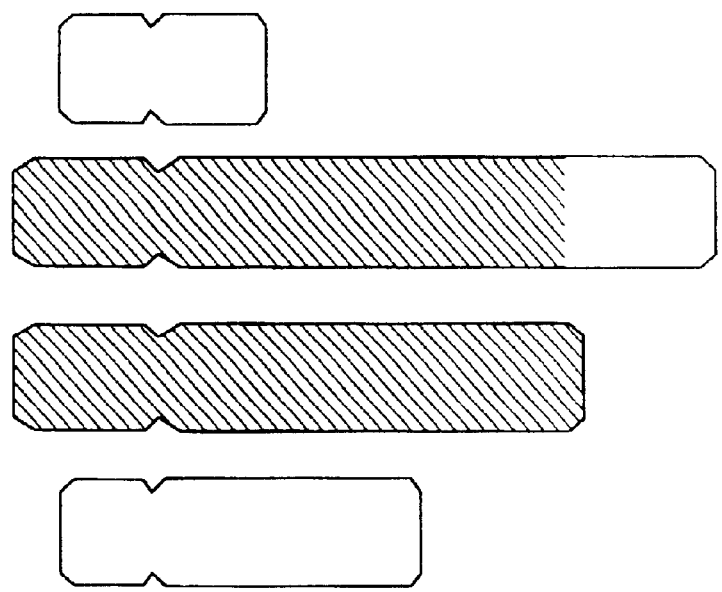
Figure 1:
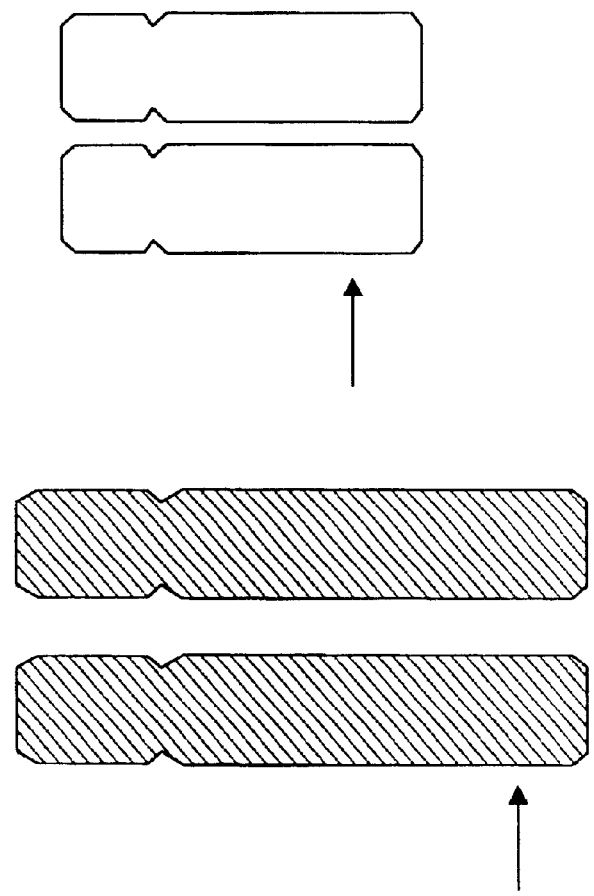

| | | | |
|---|---|---|---|
| 4,996,143 A | | 2/1991 | Heller et al. ................... 435/6 |
| 5,427,932 A | | 6/1995 | Weier et al. ............... 435/91.2 |
| 5,447,841 A | | 9/1995 | Gray et al. ..................... 435/6 |
| 5,756,696 A | * | 5/1998 | Gray et al. ................ 536/23.1 |
| 6,025,126 A | * | 2/2000 | Westbrook ..................... 435/6 |

FOREIGN PATENT DOCUMENTS

| | | |
|---|---|---|
| EP | 500290 | 2/1992 |
| EP | 0 500 290 | 8/1992 |
| WO | WO 90/05789 | 5/1990 |
| WO | WO 91/07423 | 5/1991 |
| WO | WO 93/18186 | 9/1993 |
| WO | WO 95/09928 | 4/1995 |
| WO | WO 95/09929 | 4/1995 |
| WO | WO 95/22624 | 8/1995 |

OTHER PUBLICATIONS

Cline, M., et al. (1987) "Abnormalities of Protooncogenes in Non–Small Cell Lung Cancer." *Cancer*, 60: 2669–2675.

Cremer, T., et al. (1988) "Detection of Chromosome Aberrations in Metaphase and Interphase Tumor Cells by In Situ Hybridization using Chromosome–Specific Library Probes." *Hum. Genet.*, 80:235–246.

Egli, M., et al. (1995) "A Maze Acetyl–Coenzyme A Carboxylase cDNA Sequence." *Plant Physiol.*, 108:1299–1300.

Erikson, J., et al. (1986) "Heterogeneity of Chromosome 22 Breakpoint in Philadelphia–Positive Acute Lymphocytic Leukemia." *Proc. Natl. Acad. Sci. USA*, 83: 1807–1811, Mar.

Fu, H., et al. (1995) "High–Level Tuber Expression and Sucrose Inducibility Of A Potato Sus4 Sucrose Synthase Gene Require 5' and 3' Flanking Sequences and the Leader Intron." *The Plant Cell*, 7:1387–1394.

Gornicki, P., et al. (1994) "Wheat Acetyl–Coenzyme A Carboxylase: cDNA and Protein Structure." *Proc. Natl. Acad. Sci. USA*, 91: 6860–6864.

Gray, J.W., et al. (1990) "Analytical Approaches to Detection and Characterization of Disease–Linked Chromosome Aberrations." *Bone Marrow Transplantation*, 6: 14–19.

Grossman, A., et al. (1989) "Fine Mapping of Chromosome 22 Breakpoints within the Breakpoint Cluster Region (bcr) Implies a Role for bcr Exon 3 in Determining Disease Duration in Chronic Myeloid Leukemia." *Am. J. Hum. Genet.*, 45: 729–738.

Heisterkamp, N., et al. (1983) "The Human v–abl Cellular Homologue." *J. of Mol. And Applied Genetics*, 2(1): 57–68.

Hutchins, C., et al. (1989) "Detection of Rearrangement within the Breakpoint Cluster Region of Chromosome 22 in the Diagnosis of Chronic Myeloid Leukemia." *Aust. N. Z. J. Med.*, 19: 443–448.

Kallioniemi, A., et al. (1992) "Comparative Genomic Hybridization for Molecular Cytogenetic Analysis of Solid Tumors." *Science*, 258: 818–821, Oct.

Lichter, P., et al. (1988) "Delineation of Individual Human Chromosomes in Metaphase and Interphase Cells by In Situ Suppression Hybridization using Recombinant DNA Libraries." *Hum. Genet.*, 80: 224–234.

Lichter, P., et al. (1988) "Rapid Detection of Human Chromosome 21 Aberrations by In Situ Hybridization." *Proc. Natl. Acad. Sci. USA*, 85: 9664–9668, Dec.

Lindblom, A., et al. (1993) "Deletions on Chromosome 16 in Primary Familial Breast Carcinomas are Associated with Development of Distant Metastases." *Cancer Research*, 53: 3707–3711, Aug.

Little, C., et al. (1983) "Amplification and Expression of the c–myc Oncogene in Human Lung Cancer Cell Lines." *Nature*, 306(10): 194–196, Nov.

Matthews, J., et al. (1988) "Analytical Strategies for Use of DNA Probes." *Analytical Biochemistry*, 169: 1–25.

Miura, I., et al. (1992) "Chromosome Alterations in Human Small Cell Lung Cancer: Frequent Involvement of 5q." *Cancer Research*, 52: 1322–1328.

Norman, E., et al. (1994) "Lipid Synthesis In Mycobacteria: Characterization of the Biotin Carboxyl Carrier Protein Genes from *Mycobacterium Leprae* and *M. Tuberculosis*." *J. Bacteriol.*, 176(9):2525–2531.

Oka, H., et al. (1992) "Expression of E–Cadherin Cell Adhesion Molecules in Human Breast Cancer Tissues and its Relationship to Metastasis." *Cancer Research*, 53: 1696–1701, Apr. 1993.

Page, R., et al., (1994) "Acetyl–CoA Carboxylase Exerts Strong Flux Control over Lipid Synthesis in Plants." *Biochemica et Biophysica Acta*, 1210: 369–372.

Pinkel, D., et al. (1986) "Cytogenetic Analysis Using Quantitative, High–Sensitivity, Fluoresence Hybridization." *Proc. Natl. Acad. Sci. USA*, 83: 2934–2938.

Pollard–Knight, D. (1990) "Current Methods in Nonradioactive Nucleic Acid Labeling and Detection." *J. Methods in Cell and Molecular Biol.*, 2(3): 113–132, Jun.

Sato, T., et al. (1991) "Accumulation of Genetic Alterations and Progression of Primary Breast Cancer." *Cancer Research*, 51: 5794–5799, Nov.

Sato, T., et al. (1990) "Allelotype of Breast Cancer: Cumulative Allele Losses Promote Tumor Progression in Primary Breast Cancer." *Cancer Research*, 50: 7184–7189, Nov.

Selypes, A., et al. (1988) "A Noninvasive Method for Determination of the Sex and Karyotype of the Fetus from the Maternal Blood." *Hum. Genet.* 79: 357–359.

Shorrosh, B., et al. (1994) "Molecular Cloning, Characterization, and Elicitation of Acetyl–CoA Carboxylase From Alfalfa." *Proc. Natl. Acad. Sci. USA*, 91:4323–4327.

van der Plas, D.C., et al. (1989) "Cytogenetic and Molecular Analysis in Philadelphia Negative CML." *Blood*, 73(4): 1038–1044, Mar.

Takashi, T., et al. (1989) "p53: A Frequent Target for Genetic Abnormalities in Lung Cancer." *Science*, 246:491–494, Oct.

Tkachuk, D.C., et al. (1990) "Detection of bcr–abl Fusion in Chronic Myelogenous Leukemia by In Situ Hybridization." *Science*, 250: 559–562.

Tsuda, H.,et al. (1990) "Allele Loss on Chromosome 16 Associated with Progression of Human Hepatocellular Carcinoma." *Proc. Natl. Acad. Sci. USA*, 87: 6791–6794, Sep.

Trask, B., et al. (1988) Abstract of "Fluorescence In Situ Hybridization to Interphase Cell Nuclei in Suspension Allows Flow Cytometric Analysis of Chromosome Content and Microscopic Analysis of Nuclear Organization." *Hum. Genet.*, 78(3): 251–259.

Weaver, L., et al. "Molecular cloning of the Biotinylated Subunit of 3–Methylcrotonyl–Coenzyme A Carboxylase of *Arabidopsis Thaliana.*" *Plant Physiol.*, 107:1013–1014, 1995.

Westbrook, C., et al. (1988) "Long–Range Mapping of the Philadelphia Chromosome by Pulsed–Field Gel Electrophoresis." *Blood*, 71(3): 697–702.

Westbrook, C., et al. (1992) "Clinical Significance of the BCR–ABL Fusion Genes in Adult Acute Lymphoblastic Leukemia: A Cancer and Leukemia Group B Study (8762)." *Blood*, 80(12): 2983–2990, Dec.

Westbrook, C.A. (1988) "The ABL Oncogene in Human Leukemias." *Blood Reviews*, 2:1–8.

Westbrook, C., et al. (1985) "Chromosomal Localization and Characterization of c–abl in the t(6;9) of Acute Non-lymphocytic Leukemia." *Proc. Natl. Acad. Sci. USA*, 82: 8742–8746.

Wiegant, J., et al. (1991) "In Situ Hybridization with Fluoresceinated DNA." *Nucleic Acids Research*, 19(12): 3237–3241.

Winz, R., et al. (1994) "Unique Structural Features and Differential Phosphorylation of the 280–kDa Component (Isozyme) of Rat Liver Acetyl–CoA Carboxylase." *J. Biol. Chem.*, 269(20): 14438–14445.

Yanai, Y., et al. (1995) "Genomic Organization of 251 kDa Acetyl–CoA Carboxylate Genes in Arabidopsis: Tandem Gene Duplication Has Made Two Differentially Expressed Isozymes." *Plant Cell Physiol*, 36(5): 779–787.

Yaremko, M.L., et al. (1991) Abstract of"Rapid Diagnosis of the Philadelphia Chromosome in Acute Lymphoblastic Leukemia by Direct DNA Fluorescence In Situ Hybridization." Clinical Investigation, Proceedings of the American Association for Cancer Research, 32: 164.

"Fluorescent Labeling of Human Chromosomes with Recombinant DNA Probes." *Energy and Technology Review*, Jul. 1985.

Grossman et al., "Fine mapping of chromosome 22 breakpoints within the breakpoint cluster region (bcr) implies a role for bcr Exon 3 in determining disease duration in chronic leukemia," *Am. J. Hum. Genet.*, 45:729–738, 1989.

Biennerhassett, "Clinical evaluation of a DNA probe assay for the philadelphia ($Ph^1$) translocation in chronic myelogenous leukemia," *Leukemia*, 2(10):648–657, 1988.

Trask et al., "Fluorescence in situ hybridization to interphase cell nucleis in suspension allows flow cytometric analysis of chromosome content and microscopic analysis of nuclear organizatin," *Hum. Genet.*, 78(3):251–259, 1988.

Erickson et al., "Heterogeneity of chromosome 22 breakpoint in Philadelphia–positive ($Ph^+$) acute lymphocytic leukemia," *Proc. Natl. Acad. Sci. USA*, 83:1807–1811, Mar. 1986.

Miura et al., "Chromosome alterations in human small cell lung cancer: frequent involvement of $5q^1$," *Cancer Research*, 52:1322–1328, Mar. 1992.

Yaremko et al., "Rapid diagnosis of the Philadelphia chromosome in acute lympyhoblastic leukemia by direct dna fluorescence in situ hybridization," *Clinical Investigations*, 32:164, Mar. 1991.

* cited by examiner

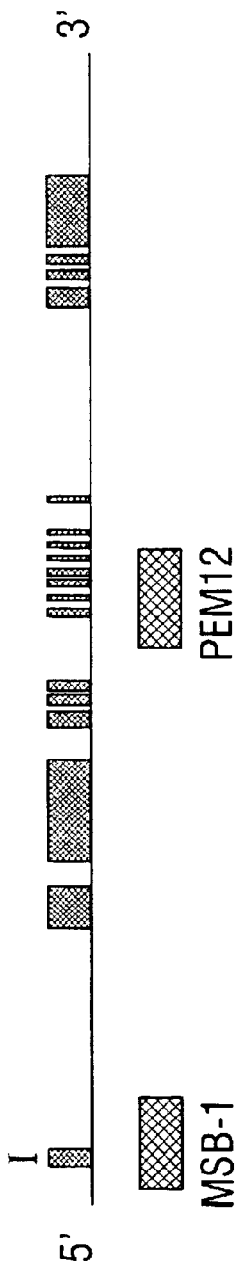
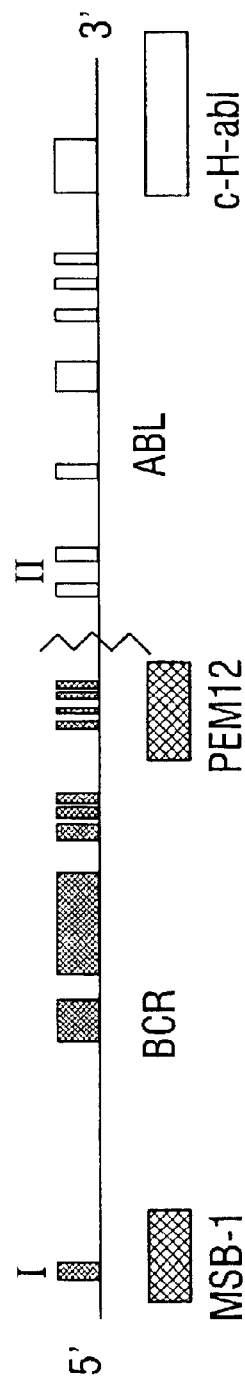
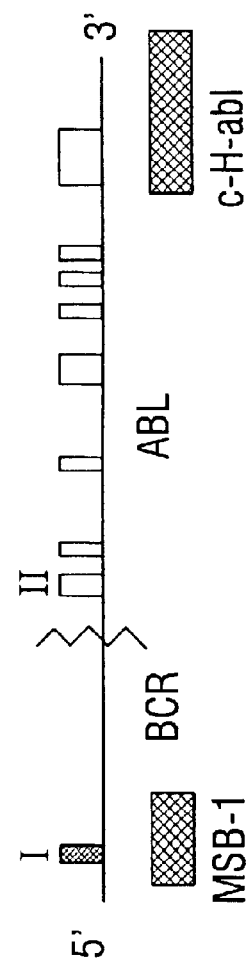
FIG. 2A
FIG. 2B
FIG. 2C

MSB-1 + c-H-abl            PEM12 + c-H-abl

MSB-1 + c-H-abl            PEM12 + c-H-abl

MSB-1 + c-H-abl            PEM12 + c-H-abl

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 1:

AGGGTGCACA GCCGCAACGG C    21

(2) INFORMATION FOR SEQ ID NO: 2:

(i) SEQUENCE CHARACTERISTICS:
      (A) LENGTH: 21 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO: 2:

CGCTTCACTC AGACCCTGAG G    21

(2) INFORMATION FOR SEQ ID NO: 3:

(i) SEQUENCE CHARACTERISTICS:
      (A) LENGTH: 19 base pairs
      (B) TYPE: nucleic acid
      (C) STRANDEDNESS: single
      (D) TOPOLOGY: linear (ii) MOLECULE TYPE: DNA -continued

```
    (xi) SEQUENCE DESCRIPTION: SEQ ID NO: 3:

GAAGGGCTTT TGAACTCTG                                                        19

(2) INFORMATION FOR SEQ ID NO: 4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO: 4:

GAAGCGCTTC TTCCTTAT                                                         18
```

METHODS AND COMPOSITIONS FOR THE DETECTION OF CHROMOSOMAL ABERRATIONS

This is a continuation of application Ser. No. 07/784,222 filed Oct. 28, 1991, now issued U.S. Pat. Ser. No. 6,025,126.

The government may have certain rights in this invention pursuant to research funding provided by the National Institutes of Health, NIH R29-CA44700.

BACKGROUND OF THE INVENTION

1. Field of the Invention

This invention relates generally to methods and compositions for direct detection of specific nucleic acid sequences associated with flanking regions of chromosomal aberration breakpoints, by forming hybrids between the sequences and genetic probes, and detecting the probes. In particular aspects, the invention concerns detection of nucleic acid sequences in situ in chromosomes, and more specifically in cells, including interphase cells. Compositions of probes useful for detecting chromosomal translocations, in particular those associated with human leukemias, are also disclosed.

2. Description of the Related Art

Substantial proportions of human diseases and malformations trace their etiology, at least in part, to genetic factors. Some of these factors are present in the zygote, others occur later as somatic cells form. Detection of genetic factors associated with particular diseases or malformations provides a means for diagnosis and treatment. For some conditions, early detection may allow prevention or amelioration of the devastating courses of diseases.

One class of genetic factors are chromosomal aberrations, that is, deviations in the expected numbers and structure of chromosomes for a particular species, and for particular cell types within a species. These may be constitutive i.e. present in the zygote, or induced post-zygotically in somatic (non-germinal cells) leading to mosaicism, that is a condition where both normal and abnormal cells are present. Chromosomes are the microscopically visible entities that are composed of the genetic material and, in higher organisms such as man, proteins and RNA. The study of chromosomes is called "cytogenetics".

There are several classes of structural aberrations that may involve autosomes or sex chromosomes or both. These aberrations are detected by noting changes in chromosome morphology (band patterns). The band patterns may be only changed in one chromosome (intrachromosomal) or in more than one chromosome (interchromosomal). Normal phenotypes may be associated with these rearrangements if the amount of genetic material has not been altered, but physical or mental anomalies are expected if there is gain or loss of genetic material. Simple deletions (deficiencies) refer to loss of part of a chromosome. Duplication refers to addition of material to chromosomes. Duplication and deficiency of genetic material can be produced by simple breakage of chromosomes, by errors during DNA synthesis, or as a consequence of segregation of other rearrangements into gametes.

Translocations are interchromosomal rearrangements effected by breakage and transfer of part of chromosomes to different locations. In reciprocal translocations, pieces of chromosomes are exchanged between two or more chromosomes. Generally, the exchanges of interest are between nonhomologues. If all the original genetic material appears to be preserved, this condition is referred to as balanced. Unbalanced forms have duplications or deficiencies of genetic material associated with the exchange; that is, something has been gained or lost "in the shuffle."

One of the most exciting associations between chromosomal aberrations and human disease, is that between chromosomal aberrations and cancer. These aberrations are generally not constitutive, i.e., present in the zygote, therefore are not present in all cells—only the abnormal ones. A mosaic condition is said to exist. For example, the Philadelphia (Ph[1]) chromosome is an important cytogenetic finding in chronic myelogenous leukemia (CML) and acute lymphoblastic leukemia (ALL). This chromosome was originally identified as a chromosome sized slightly smaller than a "G-group" chromosome. It was believed to be a deleted chromosome until detection of a reciprocal translocation between chromosomes No. 9 and 22 was reported by Rowley. A reciprocal translocation is one caused by breakage of at least two chromosomes and reunion of the broken piece in new locations.(FIG. 1) This aberration was first found to be associated with CML, but is now known to have prognostic and diagnostic value for many hematopoietic malignancies, e.g. ALL.

It is not only the translocation per se that is of clinical interest, but rather the resulting fusion of the proto-oncogene abl from the long arm of chromosome 9 with the bcr gene of chromosome 22, a consistent finding in CML. This genetic change leads to formation of a bcr-abl transcript that is translated to form a 210 kD protein present in virtually all cases of CML. This fusion can be detected by Southern analysis for bcr rearrangements or by in vitro amplification (PCR) of a complementary DNA (cDNA) transcript copied from CML mRNA. In approximately 95% of cases, the fusion gene results from a reciprocal translocation involving chromosomes 9 and 22, producing a cytogenetically distinct small acrocentric chromosome called Ph[1]. In the remaining cases the genetic rearrangement is more complex, and the involvement of the bcr and abl regions of chromosomes 9 and 22 may not be apparent during analysis of banded metaphase chromosomes. Southern blots, PCR, and metaphase chromosome banding analysis provide complementary, but incomplete, information on CML. They do not permit a genetic analysis on a cell by cell basis in a format in which the results can be related to cell phenotype as judged by morphology or other markers. Thus, assessment of the distribution of the CML genotype among cells of different lineage and maturity has not been possible.

As an example of the prognostic value of chromosomal aberrations, in adult ALL, the Ph[1] chromosome is present in up to one-third of cases, and is associated with a high relapse rate and short survival. In pediatric ALL it is much less common, but it remains one of the few chromosomal abnormalities that continues to carry a poor prognosis in spite of newer, more intensive approaches to treatment. The accurate detection of the Ph[1] is thus an important part of the diagnostic evaluation of patients with ALL.

Unfortunately, the cytogenetic diagnosis of the Ph[1] chromosome in ALL has been limited. Cytogenetic analysis has a high failure rate in this disease, compared to other acute leukemias or to CML. Fewer than 70% of cases have adequately banded chromosomes at metaphases in most reports. "Banding" is a morphological pattern revealed by treating chromosomes to reveal horizontal stripes which vary in width and staining intensity and are characteristic of specific chromosomal regions. As an alternative to cytogenetic analysis, recently, newer methods of chromosomal in situ hybridization with non-isotopically labelled genetic probes have improved and extended the capabilities of cytogenetics. One of these methods is fluorescence in situ hybridization (FISH). In this method, probes are labelled with fluorescent signals that are detectable, generally by microscopic viewing of colors. Probes are nucleic acid sequences which bind to matching (homologous) sequences, e.g. on chromosomes. Although based on cytogenetic diagnosis, FISH may be performed on interphase cells as well as on metaphases, and may be applied directly to cells from either the peripheral blood or bone marrow without the need for banded karyotypes. The diagnostic utility of FISH with repetitive, centromeric probes in cases of leukemia has been demonstrated in previous studies.

FISH on interphase cells has proven to be a useful method for diagnosis and clinical management in hematologic diseases. However, much of this experience has concentrated on detecting numerical chromosomal abnormalities (single chromosome loss or gain), making use of chromosome-specific alpha satellite probes, which are highly-repetitive, unique sequences that occur within or near the centromere of chromosomes. The centromere is a constriction most readily visible at metaphase of cell division, which occurs at a characteristic location on each chromosome. The development of competitive hybridization methods to eliminate the signal from Alu-type repeats, and improvements in optics and reagents, have also made it possible to visualize single-copy genomic clones by FISH. However, the use of genomic clones is more difficult than the use of alpha satellite probes, because of lower signal intensity and high background. These difficulties would be offset if use of genomic clones produced improvements in disease assay specificity and were more flexible. Genomic clones are those that contain repeated sequences and non-coding sequences, that is DNA as it exists in the chromosome.

Some of the background for the present invention is as follows: single stranded synthetic DNA was developed with multiple sites are incorporated where fragments may be used as probes. (Stephensen, U.S. Pat. No. 4,681,840). Oncogenes are genes whose products have the ability to transform eukaryotic cells so that they grow in a manner analogous to tumor cells. Probes and methods for detecting chromosomal translocations are disclosed in EPO 181 635 (Groffen et al.)

Pinkel et al. (1986, 1988) and Gray et al. (1990) relate fluorescent-labeled probes for the cytogenetic analysis of chromosomes, and in situ hybridization of chromosomes at metaphase and interphase with whole chromosome-specific DNA.

In situ hybridization using a mixture of radioactive labelled probes c-abl and bcr sequences were employed on a CML patient sample. Although a translocation was said to be detected, Poisson analysis, a statistical procedure, was required to differentiate random from non-random silver grain distribution after autoradiography. (Bartram et al., 1987).

Benn et al. (1987) relates the molecular genetic analysis of the bcr rearrangement in the diagnosis of CML. Analysis involved Southern blots and radioactively labelled probes.

A single bcr-derived probe from which highly repetitive sequences were removed, was employed to detect the Ph[1] translocation in CML. Restriction fragment length polymorphisms (RFLP) were used to identified patients affected with CML. Probes were used to map the chromosome 22 breakpoints within the bcr region by Grossman et al. (1989). Two separate bcr-specific probes were used to detect rearrangements within the bcr region. Southern blots and RFLP were employed. (Hutchins et al., 1989).

Flow cytometry has been applied to detection and characterization of disease—linked chromosome aberrations (Gray et al., 1990). There is a great need to improve methods of detecting specific chromosome aberrations. Flow cytometry requires in vitro cell culture, expensive equipment, and expertise in interpretation of statistical analyses of results. Therefore, it is not generally clinically useful.

Detection of aberrations by use of repeat sequence probes found near centromeres, generally alpha satellite probes, or whole chromosome probes not probes specific for genetic regions associated with diseases. Greater sensitivity and increased resolution is needed. Use of whole chromosome probes is generally limited to detection of aberrations that occur homogeneously in a cell population (Gray et al., 1990) and does not have the resolution to distinguish similar, but distinct breakpoints. The present invention relates methods and compositions for detection of chromosomal aberrations that need not be present in all cells of a sample. Compositions include novel probes that were specifically designed to detect the BCR-ABL fusion gene in acute and chronic leukemias e.g. CML and ALL, and to determine molecular subtypes.

Methods using a plurality of probes to provide increased sensitivity and specificity in detecting chromosomal aberrations, are also aspects of the present invention. These methods are particularly valuable in being applicable to interphase cells, thus avoiding the costly, laborious, time-consuming and often inconclusive cytogenetic analysis of metaphase chromosomes, and the expertise needed for flow cytometry. Not only are the methods of the present invention easier to use, but these methods do not require invasive or risky techniques inflicted on patients, such as bone marrow sampling. However, the methods and compositions of the present invention may also be used on metaphase chromosomes or Souther blots.

SUMMARY

Substantial proportions of human diseases and malformations trace their etiology, at least in part, to genetic factors. Some are inherited, some occur during the development and life of the organism. Cancers, for example, are associated with somatic mutations and/or chromosomal aberrations that may be specific for cancerous cells. Detection of genetic factors associated with particular diseases or malformations provides a means for diagnosis and treatment. For some conditions, early detection may allow prevention or amelioration of the devastating courses of diseases. For others, monitoring the course of the disease is useful to determine treatment strategies. The methods and compositions of the present invention provide multipronged reconnaissance into the genetic material to determine if it harbors abnormal factors.

This invention concerns genetic factors in the form of chromosomal aberrations, that is, deviations from the number and structure of chromosomes characterizing a species, and cell types within the species. In humans, for example, there are generally 46 chromosomes in somatic, i.e. non-germinal cells. These exist in 23 pairs, 22 of which are each matched by size and structural morphology. Structural morphology is revealed by a variety of methods, for example, treatment of chromosomes to form distinguishable horizontal bands. Analysis of such patterns, and comparison of the relative size of the chromosomes and positions of the centromere, a constriction visible at metaphase of the mitotic cell cycle on each chromosome, allow identification and classification of each pair. Analysis of banding patterns also permits detection of structural aberrations both between and within chromosomes.

For purposes of the present invention, structural chromosomal aberrations which comprise a breakpoint fusion region with nucleic acid sequences flanking the breakpoint fusion, are of particular interest. Flanking regions should be within 800 kb or less so that there are include a particular breakpoint, yet are far enough on either side of the fusion so that they are not included in it. An aspect of the present invention is to detection aberrations which are not detectable by conventional metaphase cytogenetics using light microscopy.

Chromosomes contain linear sequences of DNA, a nucleic acid that is the genetic determinative for most species (RNA is the genetic material in some lower organisms). Cloning technology has been developed which is capable of isolating specific genes directly from the genome.

To identify specific genes, that is, specific nucleic acid sequences, specific probes may be used that react only with the particular sequence of interest to seek it out from the vast excess of other sequences. The reaction of probes and their matching (homologous) sequences, is termed hybridization—the joining of the probe and its match by hydrogen bonds. Laboratory methods related to cloning technology and other techniques well known to those of skill in the art, may be found in Maniatis (1982) and in Lewin (1987). Conditions of varying stringency are used depending on the degree of homology required for a match. In examples disclosed herein, stringency conditions are set forth that are specific for hybridization to unique breakpoint provided in preferred embodiments.

The power of this approach in cytogenetic analysis comes from the increasing availability of chromosome- or locus-specific-nucleic acid probes. These fall into three general classes: 1) probes for sequences that are present in many copies on one chromosome, 2) composite probes composed of many individual elements that are homologous to target sequences distributed more-or-less continuously along an entire chromosome, and 3) probes homologous to a specific chromosome subregion or locus; for example, associated with a genetic disease. To use probes to detect chromosomal aberrations formed by breakage and reunion of, e.g., two chromosomes from different pairs (non-homologous), by probing the sequence at the fusion of the breakpoints themselves, may provide a weak signal by which the hybridization is detected. This is because when a short sequence hybridizes, the signal may be too weak to be detected. If a probe is lengthened to provide greater signal intensity, it may become too large. This will be seen as a diffuse signal. Those of skill in the art will readily determine optimum probe size for a particular application using the guidelines disclosed herein.

A laboratory procedure that produces increased specificity and low background, and one in which individual probes can be distinguished as separate entities, is preferred. Thus, the labelling of probes is not amenable to current radioactive isotopic labels, but is more suitably performed with fluorescent and other non-isotopic, i.e. enzymatic or chemical labeling methods. For diagnosis using interphase cells, that stage of cell division that most somatic cells sampled clinically are in, these labelling methods provide good enough intensity to be detectable.

An upper limit on probe size for purposes of the present invention is believed to be about 200 kb of nucleic acids, that is, about 3 times the size used in the examples disclosed herein. A goal in determining suitable sizes for probes is to detect doublets. Doublets are pairs of distinct probes in closer proximity than expected based on there normal chromosome locations in the absence of aberrations. To overcome limitations inherent in some other techniques, this invention provides a strategy of multiple sorties into the genetic material using at least two probes for separate, but related sequences; for example, one for each of the flanking regions of a breakpoint at which fusion of two chromosomal segments has occurred. Moreover, this invention takes advantage of probes large enough to give an intense signal yet specifically targeted to a genomic sequence. To be distinguishable yet juxtaposed at interphase, labelled flanking regions have to be approximately within 800 kb.

The probes are preferably labelled so that their location in the genetic material may be determined. The location is generally determined by use of a microscope. To avoid increased time and the usual problems and risks associated with radioactive labels, fluorescent labels are preferred. A separate color for each independent probe provides the most information. e.g. red on one probe, green on the other.

The probes may be detected in situ, that is, without extraction of the genetic material. In general, it will be the cell, or, more specifically, the cell nucleus that will be viewed.

Although the cells may be analyzed in metaphase, a stage in cell division wherein the chromosomes are individually distinguishable due to contraction, the methods and compositions of the present invention are particularly useful for interphase, a stage in cell division wherein chromosomes are so elongated that they are entwined as is a bowl of spaghetti, and cannot be individually distinguished. At this stage the chromosomes may be referred to as chromatin.

An additional aspect of the invention is the use of genomic DNA fragments as probes, rather than fragments which correspond simply to transcribed/translated regions. By employing genomic fragments of up to 100 kb, e.g., through the use of cosmid clones, it is possible to obtain much greater relative degree of hybridization with the chromosomal DNA, a particular advantage where a light-microscopic detection is envisioned such as in the preferred method in the present invention.

Using multiple probes, each with a distinguishable label, the overall pattern of the probes is used to assay for a breakpoint. Because allelic genes exist on chromosome pairs, each labelled probe capable of hybridizing to a sequence normally present on a specific chromosome, appear twice. If one member of each of two chromosomes is involved in a translocation which moves the sequences hybridizing to the probes together on one fusion chromosome, two of the different colored probes will be in closer proximity to each other than expected if they maintain their original chromosome location, the other two will be more distant.

In particular aspects of this invention, specific disease entities are analyzed. The hematological malignancies provide illustrative embodiments as disclosed in the following sections. One of the most clinically useful assays for chromosomal aberrations is cytogenetic analysis directed at detection of the Philadelphia chromosome (Ph[1]) which is associated with chronic myelogenous leukemia (CML), and other hematological malignancies. The presence or absence of the Ph[1] chromosome is a major diagnostic and prognostic aid. However, detection by cytogenetic analysis and other available techniques is time consuming, laborious, and not completely accurate.

An aspect of the present invention concerns the use of DNA probes for the direct detection of Philadelphia chromosomes in metaphase and interphase cells using non-radioactive methods. The so-called Philadelphia chromosome is a chromosomal aberration which results from a translocation between chromosome 9 and 22 which produces a longer chromosome 9 and shorter chromosome 22. The shortened chromosome 22, termed $Ph^1$, is generally diagnostic of certain types of leukemia, including in particular chronic myelogenous leukemia (CML), as well as various other leukemias. On a molecular level, it has been shown that the development of the $Ph^1$ chromosome includes a translocation of a portion of the c-abl oncogene into a breakpoint cluster region (bcr) of chromosome 22, which can activate the ABL gene.

A variety of molecular methods are known for diagnosing this abnormality in DNA or RNA extracted from cancer cells. The method of the present invention involves the use of a specific set of DNA probes, some corresponding to the abl gene, and some corresponding to the bcr gene. This specific set of probes is hybridized in situ to fixed cells of a sample from an individual suspected of being affected. The ABL and BCR specific probes are preferably labeled with separate fluorescein tags (e.g., biotin plus fluorescein-labeled avidin, or digoxigenin-labeled probes). Therefore, upon hybridization, both sets of labeled probes will hybridize to an a translocated chromosome 9 producing a two color doublet, whereas only the ABL specific probe will hybridize to chromosome 9 in non-affected individuals. The use of a visually detectable label allows a means of assessing the presence of the $Ph^1$ chromosome through the application of light microscopy, providing a significant advantage in terms of expertise required to carry out the assay. The methods are simpler and more rapid than previously available.

Probes developed as an aspect of the present invention include three probes that are particularly useful for detection of hematopoietic malignancies, notably chronic myelogenous leukemia (CML) and acute lymphoblastic leukemia (ALL). The novel probes are designated: PEM12, c-H-abl and MSB-1. These probes are specific for regions of the BCR gene (MSB-1 and PEM12) and a region at the ABL gene (c-H-abl). The BCR and ABL regions are those which flank the breakpoint fusion region in the $Ph^1$ chromosome associated with leukemias.

FISH was used to detect the $Ph^1$ chromosome or its genetic equivalent as the fusion of BCR and ABL probes labeled with two colors. The method was successfully used in interphase cells of ALL patients. This method, using only two probes, only detects the p210 subtype of BCR-ABL gene fusions, whereas the majority of $Ph^1$-chromosome-positive ALL cases contain the p190 fusion. For this reason, a combination of three probes used in pairs was developed that could detect both the p190 and p210 molecular subtypes. Methods using these combined probes are useful for $Ph^1$ chromosome detection by FISH in ALL. Capabilities and limitations of probes and combinations of probes in the clinical setting were assessed and shown to provide improvements over previous assays for leukemias, in particular cytogenetic analysis of metaphase chromosomes. Although the embodiments herein relate to detection of chromosomal aberrations in leukemias, the probes may be specifically tailored to meet clinical needs for the diagnosis of any chromosomal aberration, as they have for translocations in leukemias. It is only necessary to be able to determine breakpoint regions and to develop probes to those regions.

The Philadelphia ($Ph^1$) chromosome is also an important prognostic indicator in acute lymphocytic leukemia (ALL). Present in 30% of adult and 5% of pediatric cases, its presence portends a short remission duration and poor survival, despite improvements in therapy as in CML. It is a derivative of a translocation between chromosomes 9 and 22, and results in the fusion of a part of the ABL proto-oncogene on 9q with part of the BCR gene on chromosome 22. Molecular analysis shows it is much more heterogeneous because the BCR breakpoints are variable. Cytogenetic diagnosis of the $Ph^1$ chromosome in ALL is possible in only 70% of cases because of the failure to obtain adequate metaphases. The new technique of fluorescence in situ hybridization (FISH) offers the advantage of allowing the diagnoses of chromosomal abnormalities in interphase cells, thus overcoming the problem of metaphase preparations.

Using dual-color FISH with probe combinations specifically tailored to flank the breakpoints in the two types of the BCR-ABL fusion genes p210 and p190, the presence or absence of the $Ph^1$ chromosome in interphase cells was determined from 5 ALL patients, two ALL-derived cell lines, and normal lymphocytes and specified its molecular subtype when present. The method proved accurate for detection in all cases and for subtyping in 7 of 8 of the cases examined. The sensitivity and specificity for assessing the $Ph^1$ status of individual cells were low, but results were unequivocal when several cells were examined in a sample.

As can be seen from the following descriptions and examples, the methods disclosed may be performed by a pathologist on routine examination of blood and tissue samples.

FIGURES

FIG. 1: is a schematic representation of a reciprocal translocation between chromosomes No. 9 and 22.

FIG. 2: is a schematic representation of the location of probes used for dual-color FISH on the normal BCR gene and on BCR-ABL fusion gene subtypes.

FIG. 3: illustrates expected signal (labelling) patterns associated with different molecular subtypes of the $Ph^1$ in interphase cells using two-color FISH with two different probe combinations used.

Figure 4:
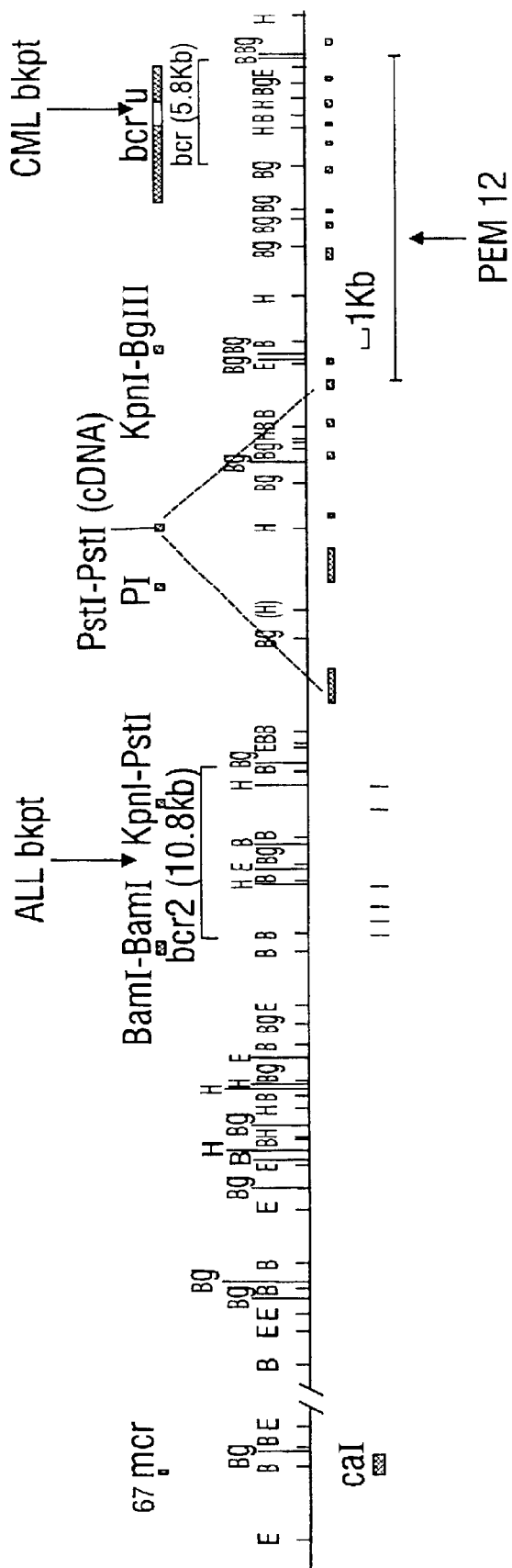

FIG. 4: is a restriction enzyme map of part of the human BCR gene from chromosomal 22.

Figure 5:
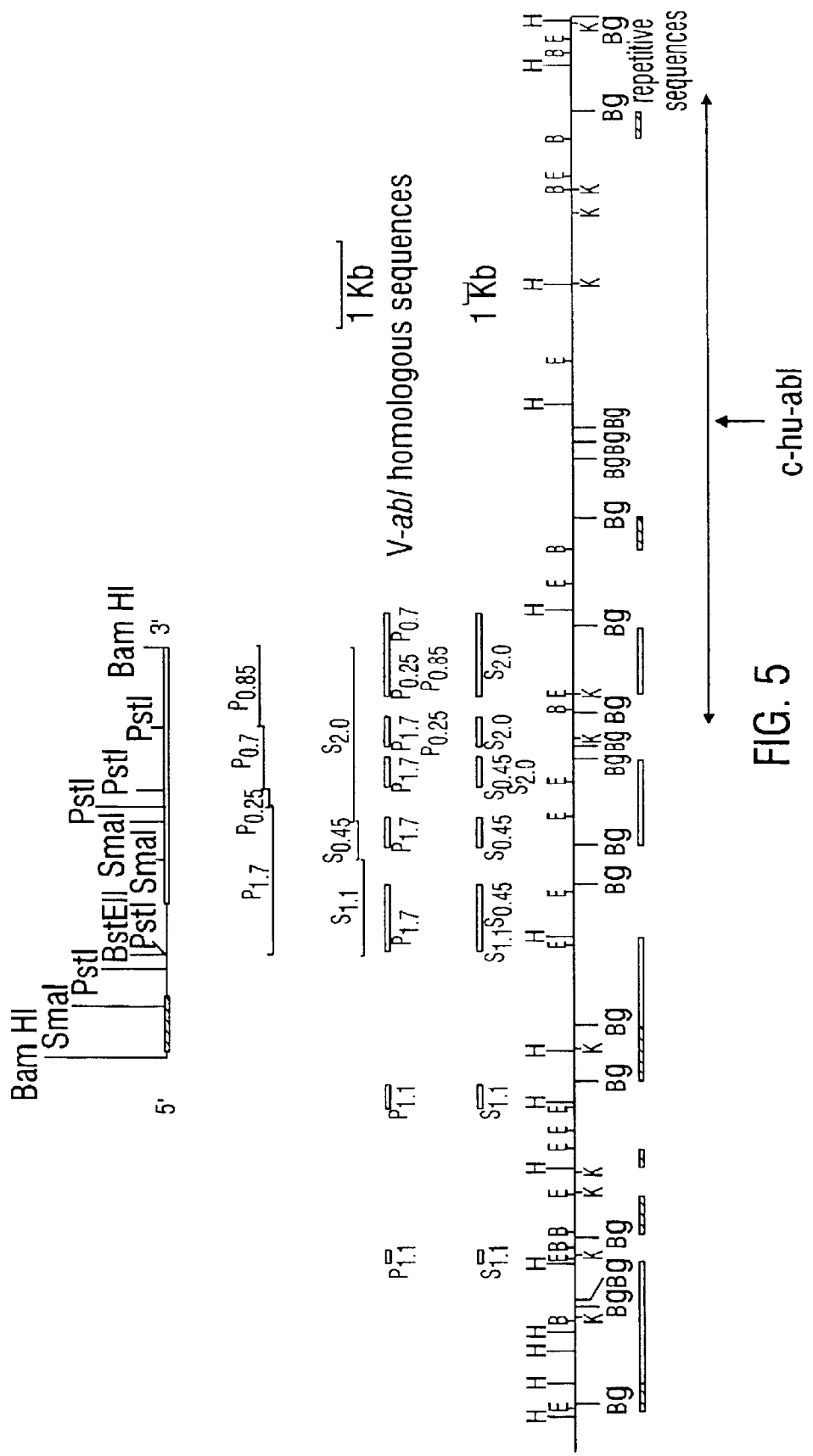

FIG. 5: is a restriction enzyme map of the human c-abl region from chromosome 9.

DETAILED DESCRIPTION OF THE INVENTION

The following examples, materials and methods provide embodiments of the invention.

EXAMPLE 1

Detection of $Ph^1$ IN CML

Two-color FISH with the abl (red) or bcr (green) probe to normal $G_1$ interphase nuclei in most cases resulted in two red and two green hybridization signals that were well separated and randomly distributed around the nucleus. In a few cells, two doublet hybridization signals were detected, probably as a result of hybridization to both sister chromatids of both homologs in cells that had replicated this region of DNA (those in the S or $G_1$ phase of the cell cycle).

Depending on the exact positioning of the breakpoints in the leukemic clone, the genetic rearrangement of CML brings the binding sites of the bcr and abl probes to within 25 to 225 kb of each other on an abnormal chromosome. Dual-color hybridization with abl and bcr probes to interphase CML cells resulted in one red and one green hybridization signal located randomly in the nucleus, and one red-green doublet signal in which the separation between the two colors was <1 μm. In some cases, the red-green doublet appeared yellow. The randomly located red and green signals are likely due to hybridization to the abl and bcr genes on the normal chromosomes, and the red-green doublet signal to hybridization to the bcr-abl fusion gene. The distance between the red and green components of the fusion signal is consistent with interphase mapping studies. Those studies have shown that DNA sequences separated by less than 250 kb should be within 1 μm of each other in two-dimensional interphase nuclei. Since the positions of the bcr and abl hybridization sites are distributed apparently randomly over the two-dimensional nucleus images in normal cells, it is not surprising that some normal cells will have red and green signals separated by <1 μm. Such false positive cells were found at a frequency of about 1% (9 of 750 cells pooled from four normal individuals). The highest frequency of false positive fusion signals for an individual case was 3 of 150 cells analyzed. Thus, with the use of this probe placement strategy, these results set a practical limit of about 1% for the detectable frequency of CML cells in a population.

Hybridization results for seven samples from six CML cases and data from PCR, Southern, and chromosome banding analysis are presented in Table 1. In all six cases red-green hybridization signals separated by <1 μm in more than 50% of nuclei were present. This was the case in three cases found to be $Ph^1$-negative by banding analysis (CML-4, CML-5, and CML-6). In most cases, the fusion event was visible in virtually every cell. One case (CML-6) showed fusion signals in almost every cell despite the fact that PCR analysis failed to detect the presence of a fusion mRNA and banding analysis did not reveal a $Ph^1$. Hybridization to metaphase cells was performed in three cases (CML-1, CML-4, and CML-5). Red and green hybridization signals in close proximity on a single small acrocentric chromosome were present in all three. In two cases (CML-1 and CML-4) scored as t(9:22)(q34:q11) by banding analysis, the red-green pair was in close proximity to the telomere of the long arm of a small acrocentric chromosome as expected for the $Ph^1$.

From the results of banding analysis one case (CML-5) was suspected to have an insertion of chromosomal material at 22q11. Two-color hybridization to metaphase cells from this case showed the red-green pair to be centrally located in a small chromosome. This result is consistent with formation of the bcr-abl fusion gene by an interstitial insertion. Fusion genes are not always detectable by cytogenetic banding analysis of metaphase chromosomes.

In one case (CML-1), two pairs of red-green doublet signals were seen in 3 of 150 (2%) interphase nuclei. This may indicate a double $Ph^1$ (or double fusion gene) in those cells that was not detected by banding analysis, which was limited to 25 metaphase cells. The acquisition of an additional $Ph^1$ is the most frequent cytogenetic event accompanying blast transformation, and its cytogenetic detection may herald disease acceleration.

Samples CML-3a and CML-3b represent an analysis of peripheral blood and bone marrow, respectively, from the same patient. The percentage of bcr-abl fusion-positive cells was higher in the bone marrow than peripheral blood.

TABLE 1

A summary of cytogenetic, FISH, and other analyses of bcr-abl rearrangements in six CML cases. CML-1 and CML-5 were bone marrow samples from patients with chronic phase CML who were receiving no treatment. CML-3a and CML-3b were from peripheral blood and bone marrow, respectively, of a CML patient in blast crisis, who was receiving hydroxyurea, CML-2 was from bone marrow in a blast crisis CML patient. CML-4 was bone marrow from a CML patient in blast crisis and receiving no treatment. CML-6 was from bone marrow in a chronic phase CML patient receiving hydroxyurea. Hybridization to metaphase cells was done on cases CML-1, CML-4, and CML-5. CML-1 and CML-4 both showed fusion gene signals localized near the end of a small acrocentric chromosome consistent with a classic $Ph^1$ resulting from a reciprocal translocation. CML-5 showed an interstitial fusion signal on 22q consistent with the bcr-abl fusion gene resulting from an insertional event. F, fusion; N, normal; D, double fusion; NI, not interpretable; and ND, not done.

| Patient | Cytogenetics | Interphase FISH | Other Analysis |
|---|---|---|---|
| CML-1 | 46, XX, t(9; 22)(q34; q11) | 80% F<br>2% D<br>18% NI | ND |
| CML-2 | 46, XY, t(9; 22)(q34; q11) | 60% F<br>40% NI | PCR[b] |
| CML-3a | 46, XY, t(9; 22)(q34; q11) | 75% F | PCR[a] |
| 25% N | | | |
| CML-3b | 46, XY, t(9; 22)(q34; q11) | 100% F | PCR[a] |
| CML-4 | 47, XY, +8, del(22)(q11) | 100% F | PCR[b] |
| CML-5 | 46, XY, ins(22; 9)(q11; q34q34) | 100% F | PCR[b] |
| CML-6 | 46, XY, t(5; 9)(q13; q34) | 100% F | PCR[b]<br>Southern[c] |

[a]See Materials and Methods, PCR, Kohler.
[b]See Materials and Methods, PCR, Hogewisch
[c]See Materials and Methods, Southern Blot.

EXAMPLE 2

Detection of $Ph^1$ in all

Location of probes used for dual-color FISH on the normal BCR gene and on BCR-ABL fusion gene subtypes is shown in FIG. 2. The normal BCR gene, and the two subtypes of BCR-ABL fusion gene are schematically represented. Black vertical bars represent BCR exons, with the first exon indicated by Roman numeral I, and the breakpoint cluster region indicated by "bcr." Open vertical bars represent ABL exons, and the second exon is indicated by Roman numeral II. The diagrams are not to scale; the approximate total distance of the BCR gene is 130 kb; the total extent of the ABL regions depicted here is 40 kb.

A. The normal BCR gene showing the approximate location of the MSB-1 probe, and the PEM12 probes (not to scale).

B. The p210 subtype of the BCR-ABL fusion gene as found on the $Ph^1$ chromosome, showing the approximate location of the MSB-1 probe and the PEM12 probe, relative to the c-H-ABL probe. The jagged line indicates a possible translocation breakpoint.

C. The p190 subtype of BCR-ABL fusion gene, with a representative breakpoint indicated by the jagged line and the approximate locations of the MSB-1 and c-H-abl probes in this gene. The breakpoint is located proximal to the PEM12 probe, and it therefore translocates to the 9q+ chromosome and is separated from the ABL sequences.

Detection of the Ph[1] in interphase cells using two-color FISH with probe combinations used and expected signal patterns given by different molecular subtypes is shown in FIG. 3. Open circles represent the green signal of fluorescein-conjugated anti-digoxigenin antibodies to detect the MSB-1 or PEM12 probes and hatched circles represent the red signal of avidin — Texas red used to detect the biotinylated probe c-H-abl.

A. The p190 fusion gene will show a pattern of doublets with the MSB-1+c-H-abl combination but result in separated doublets with PEM12+c-H-abl.

B. The p210 fusion gene show doublets with both probe combinations.

C. Normal or Ph[1]-negative ALL cells show separated signals with both probe combinations.

FIG. 4: illustrates a restriction enzyme map of part of the human BCR gene from chromosomal 22. B=BAM H1; Bg=Bg111; E =EcoR 1; H=Hin dill. The dark area in brackets below the map indicates the PEM12 region, an approximately 18 kb insert in lambda phage. Arrows indicate breakpoints in ALL and CML.

FIG. 5: illustrates a restriction enzyme map of the human c-abl region from chromosome 9. The arrow below the map indicates the c-hu-abl cosmid region, approximately a 30 kb insert.

Detection of Fusion Gene Subtypes

The detection of the two BCR-ABL fusion gene subtypes is outlined in FIG. 3. The molecular basis of the Ph[1] chromosome is a translocation between the long arms of chromosomes 9 and 22, t(9;22)(q11;q34) (Rowley, 1973) (FIG. 1 where the hatched chromosome material was originally on chromosome 9, the clear on chromosome 22; after breakage and reunion, two derivative chromosomes are formed, the small being the Ph[1] chromosome which juxtaposes part of the ABL protooncogene on chromosome 9q34 (Kurzrock et al., 1988) next to part of the BCR gene on chromosome 22q11.) The resulting fusion gene is transcribed and translated to produce a chimeric protein. Two types of BCR-ABL fusion genes exist in ALL. One type has a BCR breakpoint in the limited region of the M-bcr (Groffen et al., 1984) and produces a 210 kd protein, designated p210. This is the type of fusion gene found in virtually all cases of CML. The other type of fusion gene has a BCR breakpoint in the large region of the BCR first intron, (Rubin et al., 1988; Heisterkamp et al., 1988) and it produces a 190 kd protein, p190. This type of fusion gene accounts for 75% of the Ph[1] positive cases of ALL, the remainder having the p210 rearrangement.

A map of the normal BCR gene (Hooberman et al., 1989) and the two types of fusion genes, with probe localizations, is shown in FIG. 2. The c-H-abl probe contains the last exon of the ABL gene, which is a necessary part of the BCR-ABL fusion gene. The MSB-1 probe contains the first exon of the BCR gene, while PEM12 lies immediately 5' of the M-bcr. Both the PEM12+c-H-abl and MSB-1+c-H-abl probe combinations produce doublets when a p210 type of fusion gene is present, because both of these regions of the BCR gene are retained on the Ph[1] chromosome. When a p190 fusion gene is present, however, the breakpoint exists between these two probes, so that only MSB-1 is retained on the Ph[1] chromosome to fuse with c-H-abl, while PEM12 remains on the 9q+ chromosome. Consequently, doublets are seen with MSB-1+c-H-abl but not with PEM12+c-H-abl.

In FIG. 2A, the regions of the BCR gene to which the two probes, MSB-1 and PEM12 hybridize, are shown. A labelled MSB-1 probe contacted to chromosomes which hybridized to a normal human chromosome No. 9, would be detected in association with that chromosome. Similarly, a labelled PEM12 probe would hybridize with a chromosome No. 9 and show association with it by detection of the label.

The nucleic acid sequence of the ABL gene is normally on chromosome No. 22. The probe c-H-abl will hybridize to a region of the ABL gene as shown in FIG. 2B. Also shown in FIG. 2B are the locations of the p210 subtype of the fusion gene formed after breakage and reunion of chromosomes No. 9 and 22 to form a fusion gene. This fusion gene is designated p210 because it is capable of being expressed as a fusion protein with a molecular weight of approximately 210 kd as determined by SDS gel electrophoresis.

Application of both probe combinations thus permits the both the detection of the BCR-ABL fusion gene, and specification of the subtype. A schematic diagram of expected results in interphase is shown in FIG. 3. Because the ABL breakpoint is variable, the probe separations may be from 25 to over 200 kb. In metaphase in situ hybridization, this range of distances will cause the probe signal to fuse, but in interphase in situ hybridization the two colors can be resolved.

Figure 3A:
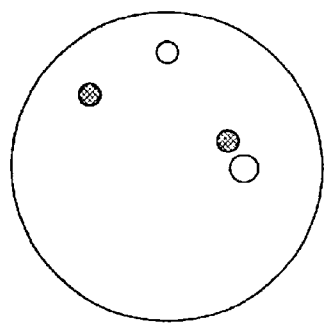
Figure 3A:
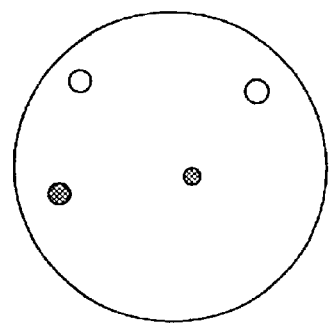
Figure 3B:
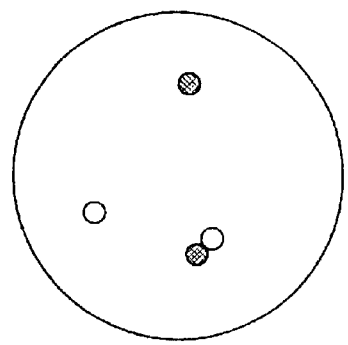
Figure 3B:
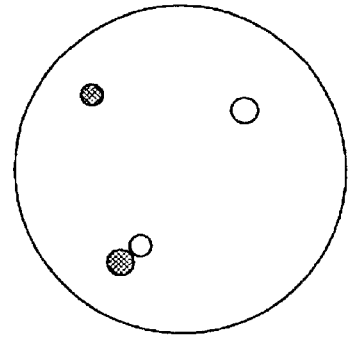
Figure 3C:
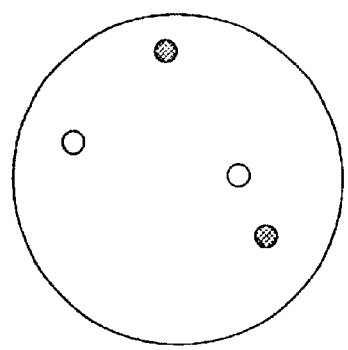
Figure 3C:
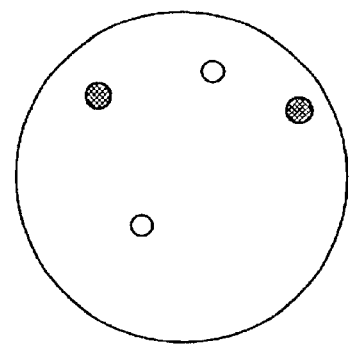

If combinations of two dual labelled probes are added to a preparation containing the p210 subtype of fusion gene, a pattern in interphase cell nuclei will appear as showing a dual labelled doublet where the fusion gene is located, and two single labels where the normal (untranslocated) chromosome Nos. 9 and 22 are located (FIG. 3B). In FIG. 3B, the appearance of doublets of MSB-1+c-H-abl, and PEM12+c-H-abl, are shown schematically.

The presence of the p190 subtype of fusion gene can be distinguished from the presence of the p210 fusion gene, or the absence of fusion genes of this type in normal cells (FIG. 3), because the p190 fusion gene does not have a PEM12 site (FIG. 2C). Therefore, as shown in FIG. 3A, labelled doublets reflecting probe associations are only expected with the combination of probes MSB-1+c-H-abl. Contacting cells with the probe combination PEM12+c-H-abl will not yield doublets, and should produce an appearance at interphase of a cell pattern undistinguishable from normal cells. (Compare FIGS. 2A and 2C).

Five cases of newly-diagnosed adult ALL, were analyzed using the methods of the present invention. Results are shown in Table 2. Cases 1 to 3 were peripheral blood samples, but all had greater than 50% blasts in the sample; cases 4 and 5 were bone marrow samples. Determination of the presence or absence of a fusion gene agreed with the molecular results in each case. The two negative cases were easily scored. Among the BCR-ABL positive cases, the subtype was obvious in patients 3 and 5, but indeterminate in patient 2. For patient 2, the MSB-1+c-H-abl determination was unequivocal, and many cells even contained two doublets; however, the result for the PEM12+c-H-abl combination was indeterminate, and no cells were observed which contained multiple doublets. Several subsequent attempts to repeat the assay with the PEM12+c-H-abl combination failed to resolve the issue.

Variability between runs was apparent. The best hybridization results allowed the interpretation of one cell in three.

Any hybridization in which no more than one cell in 8–10 showed results was discarded. Factors which affected the quality of hybridization results included quality of the sample, with best results from freshly fixed (<1 day in fixative) samples showing even, rather than clumped, chromatin condensation, and minimal residual cytoplasm. Other factors included the hybridization efficiency of the probes, and the ability to visualize the doublets, which were sometimes difficult to resolve into two different colors. The final problem was greatly improved by a change from fluorescein-tagged anti-digoxegenin Fab fragments to new, polyclonal, whole-antibody anti-digoxigenin antibodies (both by Boehringer Mannheim). Of the three probes, the c-H-abl cosmid produced the most evaluable cells, followed by PEM12, with MSB-1 as the least efficient of the probes. Of hybridizations which were discarded for failure of one probe to hybridize, the most often to fail was MSB-1.

The presence or absence of the BCR-ABL fusion gene were correctly assigned in 2 cell lines and 5 clinical specimens of ALL. The molecular subtype was easily specified for most of these cases except for case 2, in which the relatively high false positive rate (17%) made interpretation difficult.

The analysis was performed directly on interphase specimens of peripheral blood or bone marrow, obviating the need for cell culture and metaphase preparation. The ability to detect chromosomal abnormalities in interphase cells has an important impact on ALL, because failure to obtain adequate metaphases is one of the most common reasons for cytogenetic failure in this disease. Another important feature of FISH compared to conventional cytogenetics is that it directly detected the important molecular events—the BCR-ABL gene fusion subtype—rather than merely the presence of chromosomal aberration. In this regard, it compares favorably to molecular methods of diagnosis. The BCR-ABL fusion gene is an important clinical finding in ALL, and FISH is a viable option for its detection. The limitations and capabilities of the disclosed methods were evaluated in a clinical setting.

Although the ability to diagnose a case where more than one cell was available for analysis, which will generally be the situation presented, was excellent, the ability to detect the $Ph^1$ in an individual cell was rather more limited. The rate of detection of a positive signal was lower than might be predicted. In the cell lines, which are believed to contain 100% $Ph^1$ positive cells, the range of detection was 46–83% positive cells, with an overall average of 68%. In the patient samples, the average number of cells scored as positive was lower; however, these are heterogeneous populations of cells, and lower FISH results for patients relates to the lower percentage of malignant cells in the samples. There will generally be both normal and malignant cells in a sample, and the percentages will vary from patient to patient, and even within samples from the same patient.

Similarly, the rate of detection of a false positive doublet signal is 3 to 10% of cells of normal donors.

In summary, interphase detection of FISH with these probe combinations are an accurate method of detecting the presence of the $Ph^1$ chromosome in ALL, and may be a technique which will afford this diagnosis in nearly 100% of ALL patients.

EXAMPLE 3

Detection of $Ph^1$ in a Cell Line

Cell Lines and Normal Lymphocytes

The two probe combinations were tested on preparations of normal lymphocytes, a cell line with a known p210 gene fusion (BV173), and a cell line with a known p190 gene fusion (SUPB13). The results of these determinations, performed blindly, are shown in Table 3. It was found that the presence or absence of either subtype of the BCR-ABL fusion gene could accurately be assessed. However, none of the cell lines gave 100% fusion gene-positive cells, as would be expected from a homogeneous population of cells. The percent of cells scored as positive ranged from 46 to 83% of cells with recognizable signals, indicating a false negative rate of 17 to 56%. The false negatives were highly dependent on degree of background staining, sample quality, hybridization efficiency of the probes, and experience. The rate lowered as the observer became more experienced.

The false positive rate, the number of cells with doublets in normal lymphocytes, or of SUPB13 cells containing PEM12+c-H-abl doublets, ranged from 3 to 10%. Based on this experience, it was found useful to define the positive and negative patient cases relative to normal controls run at the same time. A case was defined as positive when the doublets were present at two-and-a-half times the rate found with negative controls, and as negative if the rate of doublets was similar (within 5%) to the normal lymphocyte results. Any findings in between were scored as indeterminate.

Multiple red-green hybridization sites along both arms of a single acrocentric chromosome were detected in simultaneous hybridization ions with abl and bcr probes to metaphase cells of the CML-derived cell line K-562 . Hybridization to interphase nuclei demonstrated that the red and green signals were localized to the same region of the nucleus. This is consistent with their being present on a single chromosome. Eight to 16 hybridization pairs were seen in each of 250 nuclei enumerated, indicating corresponding amplification of the bcr-abl fusion gene. Fusion gene amplification was not seen in any of the normal controls or CML patients analyzed. These findings are consistent with previous Southern blot data showing amplification of the fusion gene in this cell line.

In summary, dual-color FISH analysis of interphase cells from seven CML and four normal cell samples with abl and bcr probes suggests the utility of this approach for routine diagnosis and clinical monitoring of CML. A significant advantage of this technique is the ability to obtain genetic information from individual interphase or metaphase cells in less than 24 hours. Its application is not limited to cells that, fortuitously or through culture, happen to be in metaphase; it can be applied to all cells of a population. The genotypic analysis can be associated with cell phenotype, as judged by morphology or other markers, and this makes possible the study of lineage specificity of cells carrying the CML genotype, as well as assessment of the frequency of cells carrying the abnormality. Moreover, counting of hybridization spots allows the determination of the degree of bcr-abl gene amplification in the K-562 cell line. It is possible that this analysis may be further developed using quantitative measurement of fluorescence intensity.

TABLE 2

EVALUATION OF THE Ph[1] CHROMOSOME IN
LEUKEMIA SPECIMENS USING DUAL-COLOR FISH.

| Case | Patient Data | FISH Probe MSB1 + c-H-abl | Determinations* (combinations) PEM12 + c-H-abl | Combined FISH Results | Molecular Findings |
|---|---|---|---|---|---|
| 1. | 16F | 92/100 (8%) | 14/107 (13%) | Ph[1] negative | BCR-ABL negative |
| 2. | 63F | 36/114 (31%)** | 19/110 (17%) | Ph[1] positive indeterminate | BCR-ABL positive p190 subtype |
| 3. | 61M | 54/99 (55%) | 83/140 (59%)** | Ph[1] positive p2210 subtype | BCR/ABL positive p210 subtype |
| 4. | 39M | 2/59 (3%) | 11/118 (9%) | Ph[1] negative | BCR-ABL negative |
| 5. | 38M | 46/104 (44%) | 9/108 (8%) | Ph[1] positive p190 subtype | BCR-ABL positive p190 subtype |

*Results are presented as number of cells with doublets/total number of evaluable cells (% cells with doublets)
**Multiple doublets were observed in some cells in these cases.

TABLE 3

EVALUATION OF PROBE COMBINATIONS ON Ph[1]
CHROMOSOME-POSITIVE CELL LINES AND
NORMAL LYMPHOCYTES.

| SAMPLE | MSB-1 + c-H-abl | (%)* | PEM12 + c-H-abl | (%)* |
|---|---|---|---|---|
| SUPB13 | 1. 56/104 | (46%) | 1. 7/119 | (6%) |
|  | 2. 48/62 | (77%) | 2. 7/101 | (7%) |
|  | 3. 71/22 | (58%) |  |  |
| BV173 | 1. 80/96 | (83%) | 1. 43/73 | (59%) |
|  | 2. 76/97 | (78%) | 2. 80/102 | (78%) |
| Normal | 1. 3/120 | (3%) | 1. 8/106 | (8%) |
| Lymphocytes | 2. 12/121 | (10%) | 2. 8/109 | (7%) |

*Results expressed as number of cells with a doublet/total number of evaluable cells (percent positive cells). Each line represents a separate run.

Materials and Methods

Patient Samples

Cases were selected from newly diagnosed ALL samples referred to the inventor's laboratory for pulsed field gel electrophoresis (PFGE) and Southern molecular analysis for the BCR-ABL fusion gene. Peripheral blood was anticoagulated with EDTA (lavender-top tubes) and bone marrow with heparin (green-top tubes). Buffy coats were removed from the samples and incubated with $NH_4Cl$ (0.135M in 0.005M Tris HCl ph 7.6) to lyse red cells. After several washes in Hank's balanced salt solution (HBSS, Gibco), the cells were counted and viability assessed. Cells for FISH were allowed to "rest" in the final wash solution of HBSS for a few hours at 4° C. Cells for molecular analysis were embedded in agarose plugs according to previously described procedures. (Hooberman et al., 1989). In two cases (Patients 2 and 5), cells for FISH were thawed from liquid nitrogen storage, and incubated without stimulation or colcemid arrest for 3–24 hours prior to harvest.

Two lymphoblastoid cell lines, SUPB13 (Rubin et al., 1988), positive for the p190 type of fusion gene, and BV173 (Westbrook et al., 1988), positive for p210, were used. They were grown in RPMI 1640 (Gibco) with 10% fetal bovine serum and penicillin-streptomycin (Sigma, St. Louis, Mo.). Peripheral blood lymphocytes, obtained from normal healthy donors were stimulated with phytohemagglutinin (PHA, 1 mg/ml, Burroughs-Welcome) and cultured for 72 hrs. Cell lines and stimulated lymphocytes were incubated at 37° C. in 5% $Co_2$. Twenty-five and 5 minutes prior to harvest, Colcemid (Gibco) was added to the culture flasks to a final concentration of 0.1 ug/ml to produce metaphase arrest.

Probes

1. Description

PEM12 is a phage clone containing an 18 kb human genomic insert in EMBL3. It contains part of a sequence of the major breakpoint cluster region (M-bcr) of chromosome 22 and extends 5' of it. M-bcr is an area wherein breakpoints cluster within the BCR gene.

The c-H-abl probe is a cosmid approximately 40 kb in size with a 35 kb human insert in pCV105, and 5 kb of vector, specific for the 3' end of the ABL gene. The cosmid was isolated from a cosmid library 105SL/108K provided by Dr. Chris Y-F Lau. This library is generally available for research use and has been described in *Proc. Natl. Acad. Sci. USA* 80:5225 (1983). Cosmids were hybridized with probes containing contiguous fragments of the genes of interest, here the ABL gene sequences. The procedure was to use probes of increasing size.

MSB-1 is a phage clone with an 18 kb fragment of human DNA from the first exon of the BCR gene cloned into EMBL3.

The PEM12 and MSB-1 probes were labeled with digoxigenin-11-dUTP (Boehringer Mannheim) and the c-H-abl cosmid was labeled with biotin-11-dUTP (ENZO) by nick translation, using reagents supplied by ENZO Diagnostics. The probes were combined with each other in two combinations: MSB-1+c-H-abl and PEM12+c-H-abl. Fifty ng of c-H-abl was combined with 150–170 ng of PEM12 or MSB-1 and 1 μg of human placental DNA. The mixture was brought to a total of 10 μg of DNA/per slide with salmon sperm DNA. The probe combinations were then ethanol precipitated and redissolved in a hybridization solution of 50% formamide/10% dextran sulfate in 2×SSC, heated to 70° C. for 5 min., then incubated at 37° C. for 15–30 min. prior to application to slides.

2. Preparation

The Sequence of the BCR and ABL genes are available in the GeneBank.™ The sequences selected for use as probes may be amplified, e.g., by PCR which is well known to those of skill in the art, and used to screen libraries. (Maniatis, 1982).

Ranges of preferred probe sizes and distances from the breakpoint-fusion area, are disclosed in previous sections.

Slide Preparation and Hybridization

Cell lines, normal lymphocytes, or patient cells were pelleted by centrifugation (1000 rpm for 10 min.), and treated with hypotonic KCl (0.075M), for 12 min. at 37° C. They were resuspended in 3:1 methanol:acetic acid for fixation, and stored at 4° C. until slides were prepared, usually one to ten days. The samples were pelleted again and washed three times in fresh 3:1 methanol:acetic acid fixative immediately prior to dropping onto slides pre-cleaned with 95% alcohol. Slides of the samples were stored desiccated at 4° C. until use.

The slides were baked on a slide warmer for 4 hrs. at 65° C. They were incubated in an RNase solution, 100 µg/ml in 2×SSC for 1 hr. at 37° C., then washed 4 times in 2×SSC, 2 min. each. Next, they were passed through a graded alcohol series (70%, 80%, 95%), 2 min. each and allowed to air dry.

Denaturation of cellular DNA was performed in 70% formamide in 4×SSC for 2 min. at 70° C., and the graded alcohol series and air drying were repeated. A gentle proteinase K digestion, 60 ng/ml in 20 mM Tris/2 mM $CaCl_2$ at 37° C. for 8 min. (Pinkel et al., 1986) was followed by a third graded alcohol series and air drying. The slides were warmed to 37° C. and held there until the probe hybridization mixture was applied. Ten µl of the probe mixture was applied to each slide, the area of hybridization was covered with 22×22 mm coverslip, sealed with rubber cement and placed on a hotplate at 90° C. for 2 min. Two slides from each case were hybridized, one for the MSB-1/c-H-abl, and one for the PEM12/c-H-abl combination.

Detection of Hybridization

Detection steps are essentially those described by Trask et al. (Trask et al., 1991) with minor modifications. Following overnight incubation at 37° C. in a moist chamber, the coverslips were removed and the slides washed 3 times in 50% formamide/4×SSC, 5 min. each at 40° C. To block nonspecific binding, the slides were incubated for 5 min. at room temperature with 100 µl of 3% bovine serum albumin (BSA) (Sigma, St. Louis, Mo.) in 4×SSC under a coverslip.

The first detection reagent, avidin-Texas red (Vector) diluted in 3% BSA/4×SSC (2.5 ug of fluorochrome per ml of diluent) was applied, the coverslip was replaced, and the slides were incubated at 37° C. for 1 hr. The slides were washed 3 times, in 4×SSC, 4×SSC/0.1% Triton X, and PN (0.1M $NaH_2PO_4$/$NaH_2PO_4$ buffer pH 8/0.1% NP-40), sequentially, for 5 min. each.

A second blocking step was performed with PMN (PN+ 5% non-fat dry milk+0.05% sodium azide, centrifuged to remove milk solids), 100 µl was placed under a coverslip for 5 min. at room temperature. The second detection and amplification reagent, anti-digoxigenin polyclonal antibody (Boehringer Mannheim) and biotinylated anti-avidin (Vector), was applied in a 1:25 dilution in PMN (100 ul/slide) and the slides were incubated again at 37° C. for 1 hr. Three washes, 5 min. each, in PN followed. The PMN block step was repeated, and the third fluorescent reagent, avidin-Texas red and fluorescein-conjugated rabbit anti-sheep antibody (Vector) a 1:50 dilution, in PMN, was incubated at 37° C for 1 hr. The final washes were PN×2, then 4×SSC/0.1% Triton X once for 5 min. A brief (1–2 min.) bath in DAPI (diamidino-2-phenyl-indole, dihydrochloride; (Sigma, St. Louis, Mo.)) 200 ng/ml in 4×SSC/ 0.1% TritonX, was followed by a rinse in 4×SSC. The slides were then coverslipped with a DABCO antifade solution (diazabicyclooctane, Sigma) (90% glycerol/ 2.3% DABCO in 20 mM Tris pH 8.0), and stored desiccated in light-tight boxes at 20° C. until reviewed (usually less than three days later).

Molecular Analysis

Molecular analysis for the presence or absence of the BCR-ABL fusion gene and its subtype was performed by a combination of pulsed field gel and Southern blot, as described previously (Hooberman et al., 1989). All cases were reviewed by one observer without knowledge of the FISH results.

Interpretation of Slides for Probe Hybridization

The slides were viewed with a Zeiss standard 16 microscope equipped for epifluorescent illumination and a set of dual band-pass filters (Omega Optical). All samples were coded so that the observer did not know the results of the molecular studies at the time of review. At least 100 interphase cells were scored for the presence or absence of a red-green doublet. A doublet was defined as red and green signals lying with a distance of 1 diameter of a signal, approximately 1 micron. Bright yellow signals which could not be resolved into red and green were not counted as doublets. A slide was discarded if failure of hybridization of one or both probes was apparent. When both probe combinations for a case had been scored, an assignment of the presence and subtype of fusion gene was made.

Hybridization of Nucleic Acid Sequences

CML-3b and CML-6: Five to ten drops of marrow diluted with phosphate buffered saline (PBS) to prevent clotting were fixed in methanol/acetic acid and dropped on slides.

CML-1, CML-2, CML-4, and CML-5: Peripheral blood or bone marrow, or both, was cultured in RMPI 1640 supplemented with 10% feral bovine serum, an antibiotic mixture (gentamicin 500 µg/ml), and 1% L-glutamine for 24 hours. Cultures were synchronized according to J. J. Yunio and M. E. Chandler, Prog. Clin. Path. 7, 267 (1977), and chromosome preparations followed L. M. Gibas and Jackson, Karyogrom 9 (1986).

CML-3a: Peripheral blood was centrifuged for 5 min. at 1100 rpm, the buffy coat was pipetted off and diluted with the same volume of PBS, spun down, fixed in methanol/ acetic acid, and dropped on slides. Hybridization followed procedures described by Pinkel et al., Proc. Natl. Acad. Sci. U.S.A. 45 9138 (1983), Trask et al., Genomics 6:710 (1989) and Lawrence, Villaive, and Singer, Cell 42, 51 (1988), with modifications.

The bcr probe was nick-translated (Bethesda Research Laboratories Nick-Translation System) with digoxigenin 11-dUTP (deoxyuridine 5'-triphosphate) (Boehringer Mannheim Biochemicals) with an average incorporation of 26%. The abl probe was similarly nick-translated with biotin-11-dUTP (Enzo Diagnostics). Cells were thermally denatured at 72° C. for 5 min., dehydrated in an ethanol series, air-dried, and placed at 37° C. A hybridization mixture (10 µl) containing each probe (2 ng/ul), 50% formamide/2×standard saline citrate (SSC) 10% dextran sulfate, and human genomic DNA (1 mg/ml, sonicated to 200 to 600 bp) was heated to 70° C. for 5 min. incubated for 30 min. at 37° C., placed on the warmed slides, covered with a 20 mm by 20 mm cover slip, sealed with rubber cement, and incubated overnight at 37° C. Slides were washed three times in 50% formamide 2×SSC for 20 min each at 42° C., twice in 2×SSC at 42° C. for 30 min. each, and rinsed at room temperature in 4×SSC. All subsequent steps were performed at room temperature.

Slides were blocked in 100 µl of 4×SSC/1% bovine serum albumin (BSA) for 5 min. under a coverslip. The biotinylated abl probe was detected by applying 100 µl of Texas red-avidin (Vector Laboratories, Inc.), 2 µg/ml in 4×SSC/1% BSA) for 45 min. The slides were washed twice for 5 min. in 4×SSC/1% Triton X-100 (Sigma). The signal was amplified by applying biotinylated goat antibody so avidin (Vector Laboratories, Inc., 5 µg/ml in PNM o.1M M $NaH_2PO_4$/0.1 M $Na_2HPO_4$, pH 8 (PN) containing 5% nonfat dry milk and 0.02% sodium amide and centrifuged to remove solids), washed twice in PN for 5 min., followed by another layer of Texas red-avidin in PNM. The digoxigenin-labeled bcr probe was detected by incubation with sheep antibody to digoxigenin (obtained from D. Pepper, Boehringer Mannheim Biochemicals, Indianapolis, Ind.; 18.4 µg/ml in PNM) for 30 min, washed twice in PN for 5 min., followed by a rabbit-antibody to sheep conjugated with FITC (Organon Teknika-Cappel, 1:50 in PNM). After washing twice for 5 min. in PN, the signal wa amplified by applying a sheep antibody to rabbit immunoglobulin G(IgG) conjugated to FITC (Organon Tekniks-Cappel, 1:50 in PNM). The slides were then rinsed in PN. Slides were mounted in 10 µl of fluorescence body solution Johnson and Nogueria, J. Immunol. Methods 43, 349 (1981) containing: 4',6-amidino-2-phenylindols (DAPI) at 1 µg/ml as a counterstain.

The slides were examined with an FITC/Texas red double-band pass filter set (Omega Optical on a Zeiss Axioskap.

PCR Method of Kohler et al

The method of Kohler et al. (Leukemia 4, 8 (1990)] for bcr-abl PCR on CML-2, CML-4, and CML-5. The oligonucleotide primers used were as follows: ablX3 antisense downstream 5'-TTT CTC CAG ACT GTT GAC TGG-3'; ablX2 sense upstream 5'-CCT TCA GCG GCC AGT AGC AT-3'; CML bcr upstream 5'-ACA GCA TTC CGC TGA CCA TC-3'; CML abl antisense detection 5'-TAT GCT TAG AGT GTT ATC TCC ACT-3'.

PCR Method of Hogewisch

Method used for bcr-abl PCR by Hogewisch-Becker et al. [J. Biol. Chem. Suppl. 188, 289 (1989)] on cases CML-3a, CML-3b, and CML-6. The oligonucleotide primers used were as follows: sense primer (upstream of bcr) 5'-AGG GTG CAC AGC CGC AAC GGC-3'; antisense primer (abl)5'-CGC TTC ACT CAG ACC CTG AGG-5'; probe for the identification of bcr3/abl2 junction sequence 5'-GAA GGG CTT TTG AAC TCT G-3'; probe for the identification of bcr2abl2 junction sequence 5'-GAA GCG CTT CTT CCT TAT-3'. Exon 3 of bcr is joined to abl exon 2 if a 314-bp fragment is amplified. Exon 2 of bcr is joined to abl exon 2 if a 239-bp fragment is amplified.

Southern Blot

Southern blot analysis on case CML-4 showed a rearranged Bgl II band using an OSI Transprobe-1 Kit (oncogene Science catalog no. TP88).

Construction of a PEM Library (Maniatis, 1982)

The PEM library was made from human placental DNA. This is considered to be "normal" DNA. The DNA was prepared by partial MbaI digestion, size selection, and ligation to the vector EMBL3 at the BAMHI site.

The vector inserts in the 15–20 kb size range. The insert can be excised with SalI. The Bam site is usually lost due to ligation to MbaI.

The insert-containing phage has no EcoRI sites, whereas the wild-type phage has EcoRI sites.

Phage may be grown on NM539 media. 10–12 plates of 50,000 clones each are generally screened.

The library has been amplified. This generally leads to a titer drop of about 10-fold.

Protocol for Construction of a Cosmid Library (Maniatis, 1982)

A cosmid library was plated on amphicillin plates and amplified on chloromphenical.

Phage were grown on filters in 20 plates. The titre was about 8×10 screened colonies per plate. Normally 2–4 of a few genome equivalents were obtained.

Replica plating was performed, 2 sets of each plates were screened with a probe.

To prepare a probe, generally an insert was cut out of a plasmid so that the plasmid sequences did not cross hybridize.

An ECQ fragment 228-1-2 (a 3' probe) was made by this method. It was then nick translated. An oligonucleotide may also be prepared synthetically. The duplicate filters were treated to fix and denature them by techniques known to those of skill in the art.

Each filter was treated on a column with 0.5M NaOH 1.5M NaCl and moved to

1M TRIS ph 7.5 then into 0.5 TRIS 7.5

1.5M NaCl

Filters were blotted with 13M filter paper and dried at 68° C.

Nitrocellulase paper not nylon was preferred

A pre-hybridization mix was used to screen the library at 68° C.

The label was $7×10^6$ CPM $p^{32}$ for the probe. Hybridization was performed at 42° C.

Washed in 2×SSC 5% SDS (68%) for 2–3 hours

The filters were exposed until colonies were visible (~3 days)

Positive colonies were scored.

Colony re-purification was performed by rescreening in a similar procedure to the above.

Phage 2 clones were isolated from a phage library (human genome library of anonymous human placenta).

EMBO 1 partial digestion of DNA was performed.

DNA size was selected on a sucrose gradient to be in the 15–20 kb average size.

The fragments were ligated into the BAM HI site of the EMBO 3 vector (Stratogene or Promega).

The PEM12 clone was plated and the library screened 50,000 clones with 2 probes. The result was 2 clones.

These were screened with a BCR exon probe.

The insert was ~$16^6$ kb.

Colony Biotechnology Systems, NEM Research Products Plaque Screen Cat NEF 978/978A 978X/978Y U.S. Pat. No. 4,455,370 du Pont de Nemours.

References

The references listed below are incorporated herein by reference to the extent that they supplement, explain, provide a background for, or teach methodology, techniques, and/or compositions employed herein.

Anastasi, J., Thangavelu, M., Vardiman, J. W., Hooberman, A. L., Bian, M. L., Larson, R. A., and LeBeau, M. M. (1991), Interphase cytogenetic analysis detects minimal residual disease in a case of acute lymphoblastic leukemia and resolves the question of origin of relapse after allogeneic bone marrow transplantation. Blood 77:1087–1091.

Arnoldus, E. P. J., Wiegant, J., Noordermeer, I. A., et al. (1990), Detection of the Philadelphia chromosome in interphase nuclei. Cytogenet Cell. Genes. 54:108–111.

Bartram, et al. (1987), *Blut,* 55:505–511.

Benn, et al. (1987), *Cancer Genes. Cytogenet,* 29:1–7.

Blennerhassett, et al. (1988), *Leukemia,* 2:648–57.

Chen, S. J., et al. ( ), Molecular cloning of a 5' segment of the genomic phl gene defines a new breakpoint cluster region (bcr2) in Philadelphia positive acute leukemias. Leukemia 12:634–641.

Crist, W., Carroll, A ., Shuster, J., Jackson, J., Head, D., Borowitz, M., Behm, F., Link, M., Steuber, P., Ragab, A., Hirt, A., Brock, B., Land, V., and Pullen, J. (1990), Philadelphia Chromosome positive childhood acute lymphoblastic leukemia: Clinical and cytogenetic characteristics and treatment outcome. A pediatric oncology group study. Blood 76:489–494.

Gray, J. W. et al. (1990), Analytical approaches to detection and characterization of disease-linked chromosome aberrations, Bone Marrow Transplantation 6:14–19

Grossman et al. (1989), *Am. J. Hum. Genet.,* 45:729–38. Hooberman, A. L., Rubin, C. M., Barton, K. P., and Westbrook, C. A. (1989), Detection of the Philadelphia chromosome in acute lymphoblastic leukemia by pulsed-field gel electrophoresis. Blood 74:1101–1107. Hutchins et al. (1989), *Aust. NZ J Med.,* 19:443–448. Kurzrock, R., Gutterman, J. U., Talpaz, M. (1988), The molecular genetics of Philadelphia chromosome-positive leukemias. N. Engl. J. Med. 319-:990–998.

Lau and Kan (1983), Proc. Nat'l Acad. Sci. USA 80; 5225–5229.

Lewin, B. (1987), *Genes,* 3rd ed., Wiley and Sons, N.Y.

Lichter, P., Tang, C. C., Call, K. et al. (1990), High-resolution mapping of chromosome 11 by in situ hybridization with cosmid clones. Science 247:64–69.

Lichter, P., Cremer, T., Change, T. C., et al. (1988), Rapid detection of human chromosome 21 aberrations by in situ hybridization. Proc. Nat'l. Acad. Sci. USA 85:9664–9668.

Maniatis, T. et al. (1982), Laboratory Manual, Cold Spring Harbor, N.Y.

Pinkel, et al. (1986), *Proc. Natl. Acad. Sci. USA,* 83:2934–8.

Pinkel, et al. (1988), *Proc. Natl. Acad. Sci. USA,* 85:9138–42.

Pinkel, et al. (1990), Mutation Res. 234:303. 1990).

Tkachuk, D. C., Westbrook, C. A., Andreeff, M., Donlon, T. A., Cleary, M. L., Suryanarayan, K., Monge, M., Redner, A., Gray, J., Pinkel, D. (1990), Detection bcr-abl fusion in chronic myelogenous leukemia by in situ hybridization. Science 250:559–562.

Trask et al., (1988), *Hum. Genet.,* 78:251–9.

Trask, B., Massa, H., Kenwrick, S., and Gitschier, J. (1991), Mapping of human chromosome Xq28 by two-color fluorescence in situ hybridization of DNA sequences to interphase cell nuclei. Am. J. Hum. Genet. 48:1–15.

Westbrook, C. A. (1988), *Blood Reviews,* 2:1–8.

---

What is claimed is:

1. A method of detecting in a sample of chromosomes a chromosomal translocation associated with cancer, wherein the translocation results in at least one fusion chromosome, said method comprising:
   (a) preparing at least a first, a second and a third genomic nucleic acid probe, said first and second probe designed to hybridize to a fusion chromosome on one side of the fusion breakpoint region, but at different locations and said third probe is designed to hybridize to a chromosome on the other side of the breakpoint fusion region, wherein said first, second and third probes are distinctly labeled so that each is distinguishable;
   (b) contacting the labeled probes in pairs wherein the third probe is a member of each pair, to the sample containing the chromosomes under conditions of appropriate stringency to allow specific hybridization of the probes to complementary sequences within the DNA of said chromosomes; and
   (c) detecting the presence of label from the three probes hybridized to the chromosomes; and
   (d) inferring the presence of the translocation from the label pattern.

2. The method of detecting a chromosomal translocation of claim 1, wherein the probes are fluorescently labeled.

3. The method of detecting a chromodomal translocation of claim 2, wherin the florescent lables are distinguishable under a microscope as different colors.

4. The method of detecting a chromosomal translocation of claim 3, wherin the florescent lables are attached to digoxigenin-11-duTP and biotin-11-duTP.

5. The method of detecting a chromosomal translocation of claim 1, wherin the first and second probes hybridize to sequences that are at least approximately 800 kb apart in a fusion chromosome from the sequence to which the third probe hybridizes.

6. The method of detecting a chromosomal translocation of claim 1, wherein the probes hybridize with chromosomal DNA in situ in cells.

7. The method of detecting a chromosomal translocation of claim 6, wherein the cells comprise those in interphase of mitotic division.

8. The method of detecting a chromosomal translocation of claim 7, wherein the probes after hybridization are juxtaposed as doublets if a chromosomal translocation is present.

9. The method of detecting a chromosomal translocation of claim 8, wherein the translocation is formed by breakpoints which occur on the long arms of human chromosomes 9 and 22.

10. The method of detecting a chromosomal translocation of claim 9, wherein the translocation breakpoints are further defined as occurring at locations t(9;22)(q11;q34).

11. The method of detecting a chromosomal translocation of claim 10, wherein the translocation breakpoints are further defined to occur in the BCR and ABL genes respectively, and a fusion gene is formed comprising portions of the BCR and ABL genes.

12. The method of detecting a chromosomal translocation of claim 6 wherein the cells comprise a sample of human tissue.

13. The method of detecting a chromosomal translocation of claim 12, wherein the human tissue sample comprises peripheral blood.

14. The method of detecting a chromosomal translocation of claim 12, wherein the human tissue sample comprises bone marrow.

15. The method of detecting a chromosomal translocation of claim 6, wherein the cells comprise a sample of cultured cells.

16. The method of detecting a chromosomal translocation of claim 1, wherein said probes comprise the inserts of MSB-1, PEM12 and c-H-abl, and said probes are contacted to chromosomes in pairs.

17. A method of dectecting a chromosomal translocation resulting in a fusion gene between BCR and ABL genes associated with cancer, said method comprising:
   (a) preparing at least three nucleic acid probes, each labeled with distinguishable label, wherein a first of said probes hybridizies to the BCR gene side of the translocation, a second of said probes hybridizes to a different part of the BCR gene than the part to which the first probe hybridized, and the third probe hybridizes to part of the ABL gene;
   (b) contacting said probes in pairs, wherein the third probe is a member of each pair to chromosomes under conditions of appropriate stringency to allow specific hybridization of the probes to complementary DNA sequences in the chromosomes;
   (c) detecting the presence of hybridized probes; and
   (d) identifying said chromosomal translocation by the labeling pattern of the probes relative to the chromosomes;
   wherein said resulting fusion gene encodes either of two proteins designated as p190 and p210.

18. The method of detecting a chromosomal translocation of claim 17, wherein the fusion gene encodes a protein designated as p190.

19. The method of claim 12, wherein the presence of said fusion gene is diagnostic for acute lymphocytic leukemia (ALL).

20. The method of detecting a chromosomal translocation of claim 17, wherein the fusion gene encodes a protein designated as p210.

21. The method of detecting a chromosomal translocation of claim 12, wherein the probes consist of those selected from PEM12, c-H-abl and MSB-1.

22. The method of detecting chromosomal translocations of claim 16, wherein a first pair comprises the inserts of MSB-1 and c-H-abl, and a second pair comprises the inserts of PEM12 and c-H-abl.

23. The method of detecting a chromosomal translocation of claim 22, wherein the first pair of probes detects a fusion gene encoding a protein designated as p190 and the second pair of probes detects a fusion gene encoding a protein designated as p210.

24. The method of detecting a chromosomal translocation of claim 23, wherein the presence of said chromosomal translocation is diagnostic for ALL or chronic myelogenous leukemia (CML).

25. The genetic probe of claim 22, wherein the probe comprises at least part of the nucleic acid sequence of the insert of MSB-1.

26. The genetic probe of claim 23, wherein the probe comprises at least part of the nucleic acid sequence of the insert of c-H-abl.

27. A method of detecting a structural chromosomal translocation comprising:
   (a) contacting probes prepared from the inserts of MSB-1 and c-H-abl with chromosomal DNA from a human subject;
   (b) contacting probes prepared from the inserts of PEM12 and c-H-abl with chromosomal DNA from the same subject;
   (c) detecting the presence of probe molecules hybridized to complementary sequences within the chromosomal DNA; and
   (d) identifying the specific chromosomal translocation present in the subject by the pattern of hybridization of the subject's chromosomal DNA with said probes.

28. The method of detecting a chromosomal translocation of claim 27 wherein the probes are fluorescently labeled.

29. The method of detecting a chromosomal translocation of claim 28 wherein each probe label is distinct from each other.

30. The method of detecting a chromosomal translocation of claim 29 wherein the fluorescent labels are distinguishable under a microscope as different colors.

31. The method of detecting a chromosomal translocation of claim 27 wherein the probes after hybridization are juxtaposed as doublets if a chromosomal translocation is present.

32. The method of detecting a chromosomal translocation of claim 27 wherein the presence of said chromosomal translocation is diagnostic for ALL.

33. The method of detecting a chromosomal translocation of claim 27 wherein the presence of said chromosomal translocation is prognostic for ALL.

34. The method of detecting a chromosomal translocation of claim 27 wherein the presence of said chromosomal translocation is diagnostic for chronic myelogenous leukemia (CML).

35. The method of detecting a chromosomal translocation of claim 27 wherin the presence of said chromosomal translocation is prognostic for CML.

36. A method of detecting a chromosomal translocation resulting in a fusion gene between BCR and ABL, said fusion gene associated with cancer, said method comprising:
   (a) preparing at least two nucleic acid probes, each labeled with a distinguishable label, wherein a first of said probes hybridizes to the BCR gene side of the translocation, and the third probe hybridizes to a part of the ABL gene;
   (b) contacting said probes to chromosomes under conditions of appropriate stringency to allow specific hybridization of the probes to complementary DNA sequences in the chromosomes;
   (c) detecting the presence of hybridized probes; and
   (d) identifying the chromosomal translocation by the labeling pattern of the probes relative to the chromosomes;
   wherein said translocation results in a fusion gene that encodes either of two proteins designated as p190 and p210.

* * * * *

UNITED STATES PATENT AND TRADEMARK OFFICE
CERTIFICATE OF CORRECTION

PATENT NO. : 6,576,421 B1
DATED : June 10, 2003
INVENTOR(S) : Carol Westbrook

It is certified that error appears in the above-identified patent and that said Letters Patent is hereby corrected as shown below:

Column 23,
Line 45, please change "wherin" to -- wherein -- and "lables" to -- labels --
Line 48, please change "lables" to -- labels --
Line 49, please change "duTP" to -- dUTP --

Column 24,
Line 24, please change "claim 10" to -- claim 9 --
Line 49, please change "hybridizies" to -- hybridizes --

Column 25,
Line 1, please change "claim 12" to -- claim 17 --
Lines 7-9, please replace claim 21 with -- A method of detecting a chromosomal translocation resulting in formation of a fusion gene, said method comprising:

(a) preparing at least two nucleic acid probes, said probes selected from the group consisting of PEM12, c-H-abl and MSB-1, wherein each probe is labeled with a distinguishable label, and wherein one of said probes hybridizes to a part of the BCR gene and another of said probes hybridizes to a part of the ABL gene;

(b) contacting said probes to a chromosome under conditions of appropriate stringency to allow specific hybridization of the probes to complementary DNA sequences in the chromosome;

(c) detecting the pattern of the labels on the hybridized probes; and (d) inferring the presence of a chromosomal translocation by detection of a fusion gene, wherein said fusion gene encodes either of two proteins designated as p190 and p210. --

UNITED STATES PATENT AND TRADEMARK OFFICE
CERTIFICATE OF CORRECTION

PATENT NO.   : 6,576,421 B1
DATED        : June 10, 2003
INVENTOR(S)  : Carol Westbrook It is certified that error appears in the above-identified patent and that said Letters Patent is hereby corrected as shown below:

Column 25,
Line 10, please replace claim 22 with
-- A method of detecting a fusion chromosome, wherein said chromosome is associated with cancer, and is formed by breakage and fusion and wherein probes are contacted in pairs to a sample containing chromosomes, said method comprising:

(a) preparing at least a first and a second pair of genomic nucleic acid probes, wherein a first pair of probes comprises the inserts of MSB-1 and c-H-abl, and a second pair of probes comprises the inserts of PEM12 and c-H-abl and wherein said probes are contacted in pairs to a sample containing chromosomes and wherein MSB-1 and PEM12 hybridize to a fusion chromosome on one side of a breakpoint fusion region and c-H-abl hybridizes to the fusion chromosome on the other side of a breakpoint fusion region, wherein said first probe and said second probe are distinctly labeled;

(b) contacting the probes to chromosomes under conditions of appropriate stringency to allow specific hybridization of the probes to complementary sequences within the DNA of said chromosomes;

(c) detecting the pattern of the probe hybridized to said chromosomes; and (d) inferring from the label pattern that a fusion chromosome is present in the sample. --

Line 21, please insert -- acute myelogenous leukemia -- before "ALL" and please replace "ALL" with -- (ALL) --
Line 23, please replace claim 25 with -- The method of claim 22, wherein the sample is human blood. --
Line 26, please replace claim 26 with -- The method of claim 22, wherein the chromosomes are in metaphase. --

UNITED STATES PATENT AND TRADEMARK OFFICE
CERTIFICATE OF CORRECTION

PATENT NO.   : 6,576,421 B1
DATED        : June 10, 2003
INVENTOR(S)  : Carol Westbrook It is certified that error appears in the above-identified patent and that said Letters Patent is hereby corrected as shown below:

Column 26,
Line 22, please replace "wherin" with -- wherein --
Line 30, please replace "third" with -- second --

Signed and Sealed this

Eighteenth Day of November, 2003

JAMES E. ROGAN
*Director of the United States Patent and Trademark Office*